US006265378B1

(12) United States Patent
Broze, Jr.

(10) Patent No.: US 6,265,378 B1
(45) Date of Patent: Jul. 24, 2001

(54) PROTEIN Z-DEPENDENT PROTEASE INHIBITOR

(75) Inventor: George J. Broze, Jr., St. Louis, MO (US)

(73) Assignee: Washington, University, St. Louis, MO (US)

( * ) Notice: Subject to any disclaimer, the term of this patent is extended or adjusted under 35 U.S.C. 154(b) by 0 days.

(21) Appl. No.: 09/695,950

(22) Filed: Oct. 25, 2000

Related U.S. Application Data

(62) Division of application No. 09/271,608, filed on Mar. 17, 1999.
(60) Provisional application No. 60/086,571, filed on May 19, 1998.

(51) Int. Cl.⁷ .................................................. A61K 38/00
(52) U.S. Cl. ............................................. 514/12; 530/350
(58) Field of Search ................................ 514/12; 530/350

(56) References Cited

FOREIGN PATENT DOCUMENTS

| 0419099 | 3/1991 | (EP) . |
| 0543240 | 5/1993 | (EP) . |
| 0551084 | 7/1993 | (EP) . |
| 9639640 | 12/1996 | (WO) . |

OTHER PUBLICATIONS

Prowse and Esnouf, *Biochem. Soc. Trans.*, vol. 5, pp. 255–256 (1977).
Mattock and Esnouf, *Nat. New Biol.*, vol. 242, pp. 90–92 (1973).
Petersen et al., *FEBS Lett.*, vol. 114, pp. 278–282 (1980).
Broze and Miletich, *J. Clin, Invest.*, vol. 83, pp. 933–938 (1984).
Miletich and Broze, *Blood*, vol. 69, pp. 1580–1586 (1987).
Sejima et al., *Biochem. Biophys, Res. Commun.*, vol. 171, pp. 661–668 (1990).
Ichinose et al., *Biochem. Biophys. Res. Commun.*, vol. 172, pp. 1139–1144 (1990).
McDonald et al., *Biochemistry*, vol. 36, pp. 5120–5127 (1997).
Broze et al., *Blood*, vol. 71, pp. 335–343 (1988).
Han et al., *Proc. Natl. Acad. Sci. USA*, vol. 95, pp. 9250–9255 (1998).
New et al., *Biochem. Biophys. Res. Commun.*, vol. 223, pp. 404–412 (1996).
Smith et al., *J. Biol. Chem.*, vol. 267, pp. 19140–19146 (1992).
Broze and Miletich, *J. Clin. Invest.*, vol. 76, pp. 937–946 (1985).
Broze, J. Clin Invest., 73. 933–938 (1984), abstract Biosis.
Ichinose, BBRC 172, 1139–1144 (1990).
Han, PNAS, USA, 95, 9250–9255 (1998).
Eckert, Circulation, 90, 1619 (1994), abstract 3337.
Kemkes–Matthes, Thromb, Res., 79, 49–55 (1995).
Richter, Ann. Hemat. 76, 25–28 (1998), abstract P 291.

*Primary Examiner*—Rebecca E. Prouty
*Assistant Examiner*—M. Monshipouri
(74) *Attorney, Agent, or Firm*—Scott J. Meyer

(57) ABSTRACT

The disclosure describes the purification and isolation of a novel human protein Z-dependent protease inhibitor (ZPI) from plasma characterized as having a molecular weight of about 72 kDa, being a single chain protein with an N-terminal amino acid sequence of LAPSPQSPETPA, and which produces a rapid inhibition of factor Xa in the presence of human protein Z (PZ), calcium ions and cephalin. The disclosure further describes the isolation and cloning of the ZPI cDNA from a human cDNA library. The ZPI cDNA is 2.44 kb in length and has an open reading frame that encodes the 423 residue mature ZPI protein and a 21 residue signal peptide. PZ, ZPI and the combination of PZ and ZPI are used to inhibit blood coagulation.

2 Claims, 9 Drawing Sheets

FIG. 6

```
                                                              ctggagtggggta 13
agaggcgaattatagacacaaggggctcctctgcaggaaggaggccaagggaaagaggcttgaaaggcttgatat 88
ttcacccaccaccactcactgccggagtaagcaggtctcccccttcccagggctgaggggaggcagggatgtgtgc 163
tgtcccagggctgagaagtggcaggtgagctggtgattccttactgcccaggttctgtctaggaaggtgcgtcct 238
caccatgctggatggtgtcctagtccaggagcacccccctgagctcctggcctagactccaaagggttgggtagat 313
gagcaaagactttacaaagaccttaggcgatatatgtccaggagcacccaggaattactgggctaccactgcaga 388
ctgcaggacaagctccaagaacaggaaggaagtcttgcagctgaagggaggcactccttggcctccgcagccgat 463
```

| cac | atg | aag | gtg | gtg | cca | agt | ctc | ctg | ctc | tcc | gtc | ctc | ctg | gca | cag | gtg | tgg | ctg | 520/-4 |
|---|---|---|---|---|---|---|---|---|---|---|---|---|---|---|---|---|---|---|---|
|  | M | K | V | V | P | S | L | L | L | S | V | L | L | A | Q | V | W | L |  |
| gta | ccc | ggc | ttg | gcc | ccc | agt | cct | cag | tcg | cca | gag | acc | cca | gcc | cct | cag | aac | cag | 577/16 |
| V | P | G | L | A | P | S | P | Q | S | P | E | T | P | A | P | Q | N* | Q |  |
| acc | agc | agg | gta | gtg | cag | gct | ccc | aag | gag | gaa | gag | gaa | gat | gag | cag | gag | gcc | agc | 634/35 |
| T | S | R | V | V | Q | A | P | K | E | E | E | E | D | E | Q | E | A | S |  |
| gag | gag | aag | gcc | agt | gag | gaa | gag | aaa | gcc | tgg | ctg | atg | gcc | agc | agg | cag | cag | ctt | 691/54 |
| E | E | K | A | S | E | E | E | K | A | W | L | M | A | S | R | Q | Q | L |  |
| gcc | aag | gag | act | tca | aac | ttc | gga | ttc | agc | ctg | ctg | cga | aag | atc | tcc | atg | agg | cac | 748/73 |
| A | K | E | T | S | N | F | G | F | S | L | L | R | K | I | S | M | R | H |  |
| gat | ggc | aac | atg | gtc | ttc | tct | cca | ttt | ggc | atg | tcc | ttg | gcc | atg | aca | ggc | ttg | atg | 805/92 |
| D | G | N | M | V | F | S | P | F | G | M | S | L | A | M | T | G | L | M |  |
| ctg | ggg | gcc | aca | ggg | ccg | act | gaa | acc | cag | atc | aag | aga | ggg | ctc | cac | ttg | cag | gcc | 862/111 |
| L | G | A | T | G | P | T | E | T | Q | I | K | R | G | L | H | L | Q | A |  |
| ctg | aag | ccc | acc | aag | ccc | ggg | ctc | ctg | cct | tcc | ctc | ttt | aag | gga | ctc | aga | gag | acc | 919/130 |
| L | K | P | T | K | P | G | L | L | P | S | L | F | K | G | L | R | E | T |  |
| ctc | tcc | cgc | aac | ctg | gaa | ctg | ggc | ctc | aca | cag | ggg | agt | ttt | gcc | ttc | atc | cac | aag | 976/149 |
| L | S | R | N | L | E | L | G | L | T | Q | G | S | F | A | F | I | H | K |  |
| gat | ttt | gat | gtc | aaa | gag | act | ttc | ttc | aat | tta | tcc | aag | agg | tat | ttt | gat | aca | gag | 1033/168 |
| D | F | D | V | K | E | T | F | F | N* | L | S | K | R | Y | F | D | T | E |  |
| tgc | gtg | cct | atg | aat | ttt | cgc | aat | gcc | tca | cag | gcc | aaa | agg | ctc | atg | aat | cat | tac | 1090/187 |
| C | V | P | M | N | F | R | N* | A | S | Q | A | K | R | L | M | N | H | Y |  |
| att | aac | aaa | gag | act | cgg | ggg | aaa | att | ccc | aaa | ctg | ttt | gat | gag | att | aat | cct | gaa | 1147/206 |
| I | N | K | E | T | R | G | K | I | P | K | L | F | D | E | I | N | P | E |  |
| acc | aaa | tta | att | ctt | gtg | gat | tac | atc | ttg | ttc | aaa | ggg | aaa | tgg | ttg | acc | cca | ttt | 1204/225 |
| T | K | L | I | L | V | D | Y | I | L | F | K | G | K | W | L | T | P | F |  |
| gac | cct | gtc | ttc | acc | gaa | gtc | gac | act | ttc | cac | ctg | gac | aag | tac | aag | acc | att | aag | 1261/244 |
| D | P | V | F | T | E | V | D | T | F | H | L | D | K | Y | K | T | I | K |  |
| gtg | ccc | atg | atg | tac | ggt | gca | ggc | aag | ttt | gcc | tcc | acc | ttt | gac | aag | aat | ttt | cgt | 1318/263 |
| V | P | M | M | Y | G | A | G | K | F | A | S | T | F | D | K | N | F | R |  |
| tgt | cat | gtc | ctc | aaa | ctg | ccc | tac | caa | gga | aat | gcc | acc | atg | ctg | gtg | gtc | ctc | atg | 1375/282 |
| C | H | V | L | K | L | P | Y | Q | G | N* | A | T | M | L | V | V | L | M |  |
| gag | aaa | atg | ggt | gac | cac | ctc | gcc | ctt | gaa | gac | tac | ctg | acc | aca | gac | ttg | gtg | gag | 1432/301 |
| E | K | M | G | D | H | L | A | L | E | D | Y | L | T | T | D | L | V | E |  |
| aca | tgg | ctc | aga | aac | atg | aaa | acc | aga | aac | atg | gaa | gtt | ttc | ttt | ccg | aag | ttc | aag | 1489/320 |
| T | W | L | R | N | M | K | T | R | N | M | E | V | F | F | P | K | F | K |  |
| cta | gat | cag | aag | tat | gag | atg | cat | gag | ctg | ctt | agg | cag | atg | gga | atc | aga | aga | atc | 1546/339 |
| L | D | Q | K | Y | E | M | H | E | L | L | R | Q | M | G | I | R | R | I |  |
| ttc | tca | ccc | ttt | gct | gac | ctt | agt | gaa | ctc | tca | gct | act | gga | aga | aat | ctc | caa | gta | 1603/358 |
| F | S | P | F | A | D | L | S | E | L | S | A | T | G | R | N | L | Q | V |  |
| tcc | agg | gtt | tta | caa | aga | aca | gtg | att | gaa | gtt | gat | gaa | agg | ggc | act | gag | gca | gtg | 1660/377 |
| S | R | V | L | Q | R | T | V | I | E | V | D | E | R | G | T | E | A | V |  |
| gca | gga | atc | ttg | tca | gaa | att | act | gct | tat | tcc | atg | cct | cct | gtc | atc | aaa | gtg | gac | 1717/396 |
| A | G | I | L | S | E | I | T | A | Y | S | M | P | P | V | I | K | V | D |  |
| cgg | cca | ttt | cat | ttc | atg | atc | tat | gaa | gaa | acc | tct | gga | atg | ctt | ctg | ttt | ctg | ggc | 1774/415 |
| R | P | F | H | F | M | I | Y | E | E | T | S | G | M | L | L | F | L | G |  |
| agg | gtg | gtg | aat | ccg | act | ctc | cta | taa | ttcaggacacgcataagcacttcgcgtgtagtagatgct | | | | | | | | | | 1840/423 |
| R | V | V | N* | P | T | L | L | *** | | | | | | | | | | |  |

```
gaatctgaggtatcaaacacacacaggataccagcaatggatggcagggagagtgttccttttgttcttaacta 1915
gtttagggtgttctcaaataaatacagtagtccccacttatctgaggggatacattcaaagaccccccagcagat 1990
gcctgaaacggtggacagtgctgaaccttatatatattttttcctacacatacatacctatgataaagtttaatt 2065
tataaattaggcacagtaagagattaacaataataacaacattaagtaaaatgagttacttgaatgcaagcactg 2140
caataccataacagtcaaactgattatagagaaggctactaagtgactcatggggcgaggagcatagacagtgtgg 2215
agacattgggcaaggggagaattcacatcctgggtgggacagagcaggacaatgcaagattccatcccactactc 2290
agaatggcatgctgcttaagactttttagattgttttatttctggaattttcatttaatgtttttggaccatggtt 2365
gaccatggttaactgagactgcagaaagcaaaaccatggataagggaggactactacaaaagcattaaattgata 2440
catatttttttaaaaaaaaaaaaaaaa
```

```
ZPI     ERGTEAVAGILSEITAYSMPP--   -VIKVDRPFHFMIYEETSGMLLFLGRVVNPTLL
RASP-1  ERGTEVVSGTVSEITAYCMPP--   -VIKVDRPFHFIIYEEMSRMLLFLGRVVNPTVL
A1AT    EKGTEAAGAMFLEAIPMSIPP--   EVKFNKPFVFLMIEQNTKSPLFMGKVVNPTQK
A1AU    EKGTEATGAPHLEEKAWSKYQ--   TVMFNRPFLVIIKEYITNFPLFIGKVVNPTQK
AT-III  EEGSEAAASTAVVIAGRSLNPNRVTFKANRPFLVFIREVPLNTIIFMGRVANPCVK
HC-II   EEGTQATTVTTVGFMPLSTQV--   RFTVDRPFLFLIYEHRTSCLLFMGRVANPSRS
PN-I    EDGTKASAATTAILIARSSPP--   WFIVDRPFLFFIRHNPTGAVLFMGQINKP
```

FIG. 8

PROTEIN Z-DEPENDENT PROTEASE INHIBITOR

This is a division of application Ser. No. 09/271,608, filed Mar. 17, 1999, pending, which claims the benefit of application Ser. No. 60/086,571, filed May 19, 1998.

This invention was made in part with government support under grant numbers HL 34462 and HL 60782 awarded by the National Institutes of Health. The government has certain rights to the invention.

FIELD OF THE INVENTION

The present invention relates to the field of vitamin K-dependent plasma proteins such as the four classical clotting factors (Factors II, VII, IX and X), protein C, protein S and, more particularly, to human protein Z (PZ).

BACKGROUND OF THE INVENTION

[Note. Literature references on the following background information and on conventional test methods and laboratory procedures well-known to the ordinary person skilled in the art, and other such state-of-the-art techniques as used herein, are indicated by numbers in parentheses and appended at the end of the specification.]

Vitamin K is required for the post-translational formation of gamma carboxyglutamic acid (Gla), which is present in a number of plasma proteins that are involved in coagulation: Prothrombin, factors VII, IX, X, protein C and protein S (1,2). Gla-mediated calcium ion binding in these proteins is necessary for their association with phospholipid surfaces and is critical for their hemostatic function (3). In 1977, Prowse and Esnouf identified an additional vitamin X-dependent protein circulating in bovine plasma and named it protein Z (PZ) (4). Initially thought to represent a single chain form of bovine factor X, bovine PZ was later identified as a discrete Gla-containing protein (5,6). The human counterpart of bovine PZ was isolated in 1984 (7).

Human PZ is a 62,000 molecular weight glycoprotein that has a plasma half-life of ~2.5 days (8). Plasma PZ levels in blood donors span a broad range with a mean concentration of 2.9±1.0 μg/mL in EDTA anticoagulated samples (corresponding to ~2.6 μg/mL in citrate plasma) (8). The amino-terminal half of PZ is very homologous (40–50%) to those of factors VII, IX and X, and contains a Gla-domain, two EGF-like domains, and a region which connects to a homologue of the catalytic domains present in the serine protease zymogens. In the carboxy-terminal domain of PZ, however, the region around the typical "activation" site is absent and the His and Ser residues of the catalytic triad are lacking (the Asp residue is conserved) (9,10).

McDonald et al (11) have recently reported that the kinetics of the binding of human and bovine PZ to phosphatidylcholine/phosphatidylserine (PC/PS=75%/25%) vesicles is different from that of the other vitamin K-dependent coagulation factors. The $k_{assn}(10^{-5}s^{-1}M^{-1})$ and $kd_{dssn}(s^{-1})$ rate constants are 1.95 and 0.0063 for bovine PZ and 3.36 and 0.057 for human PZ. In comparison the values of these constants for bovine prothrombin are 176.0 and 1.9, respectively. Thus, the association and dissociation rate constants for bovine and human PZ are dramatically slower than those of prothrombin and the dissociation of bovine PZ from phospholipids is significantly slower than that of human PZ.

BRIEF DESCRIPTION OF THE INVENTION

The invention relates to human protein Z (PZ) and a novel human protein Z-dependent inhibitor (ZPI).

In accordance with one embodiment of the invention, a novel human protein Z-dependent protease inhibitor (ZPI) has been purified and isolated from plasma and characterized structurally and biologically. ZPI is a 72,000 molecular weight, single chain protein with an initially determined N-terminal amino acid sequence of LAPSPQSPEXXA (X=indeterminant). Using the conventional three-letter amino acid symbols required by 37 CFR §1821–1.825, the N-terminal sequence is as follows:

[SEQ ID NO:1]
Leu Ala Pro Ser Pro Gln Ser Pro Glu Xaa Xaa.
1               5               10

This sequence does not match or show significant homology with the sequences accessible in publicly available protein or DNA data bases. Thus, it believed that ZPI is a novel protein.

ZPI has an estimated concentration in citrate plasma of about 1.0 to 1.6 μg/mL. In systems using purified components, the factor Xa inhibition produced by ZPI is rapid (>95% within one minute by bioassay) and required the presence of human protein Z, calcium ions and cephalin. The inhibitory process appears to involve the formation of a factor Xa-PZ-ZPI complex at the phospholipid surface.

To further characterize ZPI in another embodiment of the invention, its cDNA was isolated and cloned from a human liver cDNA library. The ZPI cDNA is 2.44 kb in length and has a relatively long 5' region (466 nt) that contains six potential ATG translation start codons. ATG's 1 to 4 are followed by short open reading frames, whereas $ATG_5$ and $ATG_6$ are in an uninterrupted 1335 bp open reading frame that includes the encoded ZPI protein. The deduced ZPI protein of 444 amino acids has a typical 21 residue signal peptide that is followed by the N-terminal sequence of the purified protein in which the initially indeterminate residues 10 and 11 in SEQ ID NO:1 are, respectively, threonine and proline, as in SEQ ID NO:8.

In vitro experiments show that $ATG_6$ is sufficient for the expression of rZPI in cultured Chinese hamster ovary (CHO) cells. Northern analysis suggests that the liver is a major site of ZPI synthesis.

The predicted 423 residue amino acid sequence of the mature ZPI protein is 25–35% homologous with members of the serpin superfamily of protease inhibitors and is 78% identical to the amino acid sequence predicted by a previously described CDNA isolated from rat liver, regeneration-associated serpin protein-1 (rasp-1).

Alignment of the amino acid sequence of ZPI with those of other serpins predicts that Tyr387 (Y387) is the $P_1$ residue at the reactive center of the ZPI molecule. Consistent with this notion, rZPI (Y387A), an altered form of ZPI in which tyrosine 387 has been changed to alanine, lacks PZ-dependent factor Xa inhibitory activity.

In still other embodiments of the invention, PZ, ZPI and the combination of PZ and ZPI are used as inhibitors of blood coagulation. As illustrated below, this is the first work showing that PZ and ZPI produce inhibition of coagulation. This work also shows that PZ can inhibit coagulation in the absence of ZPI (FIG. 5).

DETAILED DESCRIPTION OF THE INVENTION

While the specification concludes with claims particularly pointing out and distinctly claiming the subject matter regarded as forming the invention, it is believed that the invention will be better understood from the following preferred embodiments of the invention taken in conjunction with the accompanying drawings.

(▲), without cephalin, without PZ;

(○), without cephalin, with PZ;

(■), with cephalin, without PZ;

(●), with cephalin, with PZ.

Figure 2:
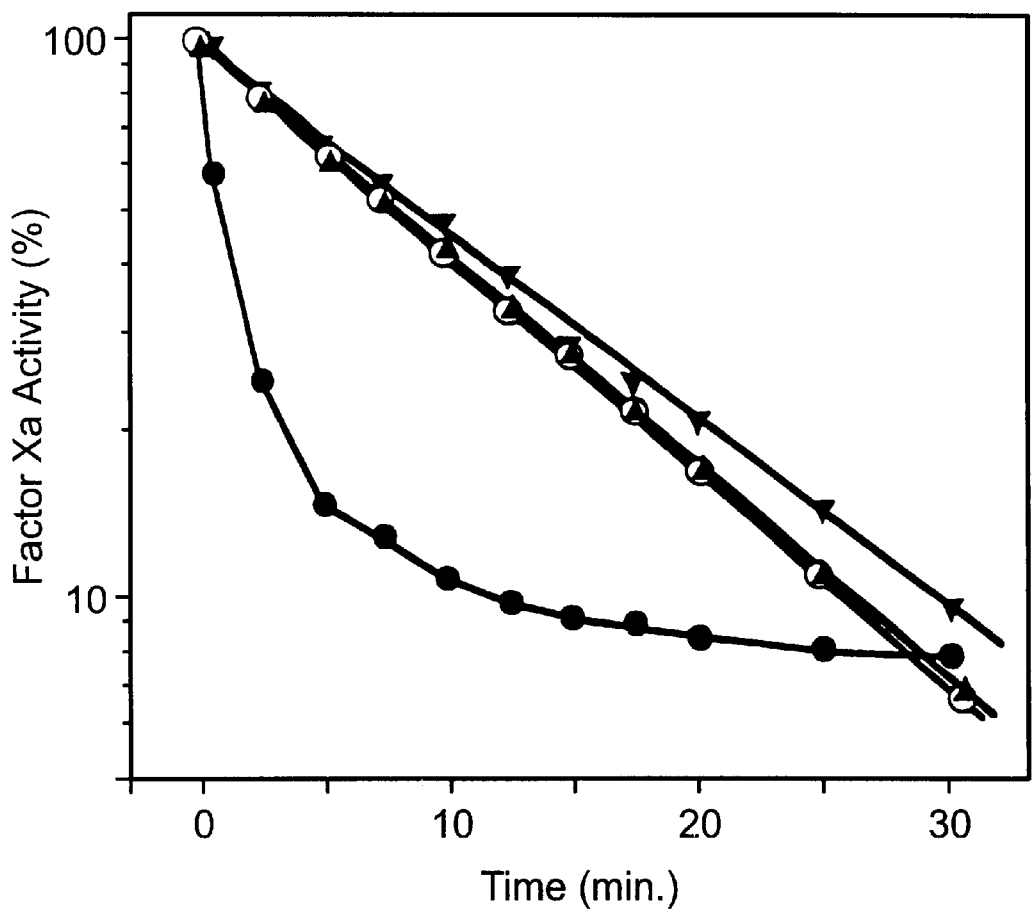

FIG. 2 is a graphical representation which shows the factor Xa a inhibition by serum. Factor Xa (5 nM), CaCl$_2$(4 mM), cephalin (15 $\mu$M) with or without PZ (40 nM) were incubated 5 min at 22° C. before the addition of barium absorbed serum (25% v/v) which had been previously treated for 30 min. with rabbit preimmune or immune anti-ZPI IgG (300 $\mu$g/mL). At the specified times thereafter, samples of the reactions were diluted in HSA with 1 mM EDTA and assayed for factor Xa activity by bioassay.

(●), with PZ and preimmune IgG;

(▼), with PZ and immune IgG;

(○), without PZ and with preimmune IgG;

(▲), without PZ and with immune IgG.

Figure 3:
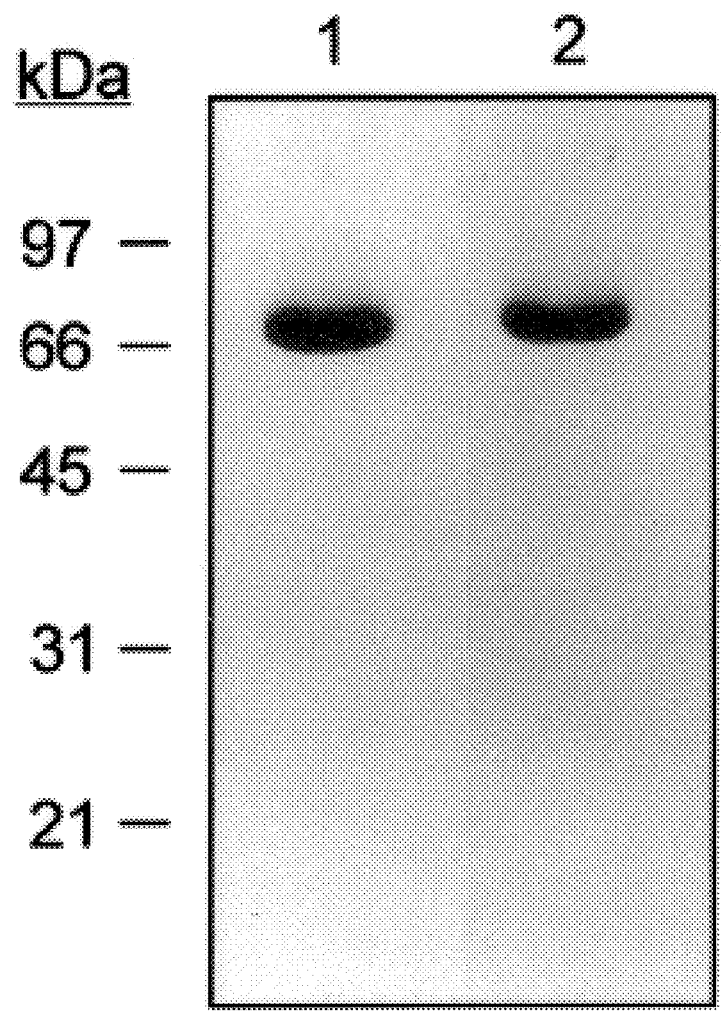

FIG. 3 shows the SDS-Page of purified ZPI. ZPI (5 $\mu$g) was analyzed with (lane 2, right) or without (lane 1, left) reduction with 5% 2-mercaptoethanol. Protein was stained with Coumassie Brilliant Blue. The position of molecular weight standards in kDa is shown on the left.

FIG. 4, in four parts, FIGS. 4A, 4B, 4C and 4D, is a graphical representation which shows the PZ-dependent inhibition of factor Xa by ZPI.

Figure 4A:
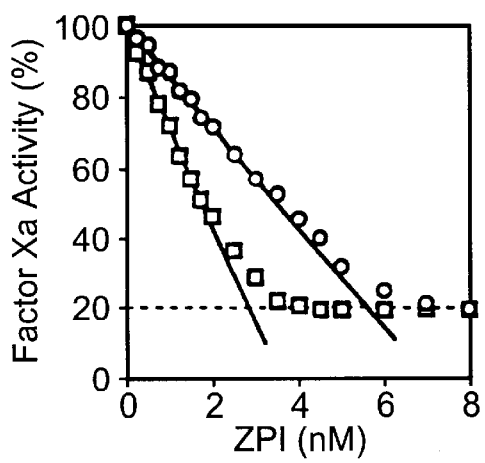

FIG. 4A shows the ZPI dose/response. Reactions containing factor Xa (2.5 or 5.0 nM), CaCl$_2$ (4 mM), cephalin (15 $\mu$M) and PZ (40 nM) were incubated with increasing concentrations of ZPI for 15 min. at 22° C. before remaining factor Xa activity was determined by amidolytic assay. The molar concentration of ZPI was estimated assuming 1.0 mg/mL ZPI produces an A$_{280}$ of 1.0. (□), factor Xa 2.5 nM; (○), factor Xa 5.0 nM.

Figure 4B:
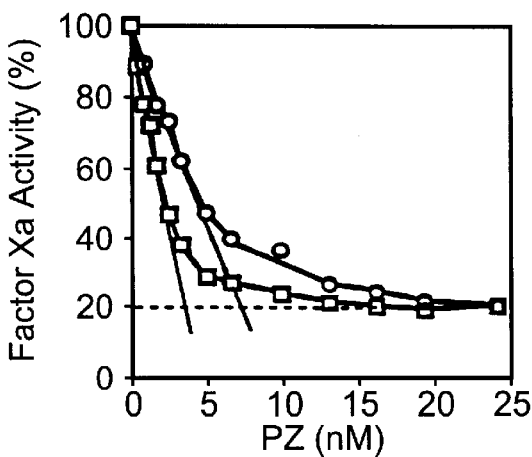

FIG. 4B shows the PZ dose/response. Reactions containing factor Xa (2.5 or 5.0 nM), CaCl$_2$ (4 mM), cephalin (15 $\mu$M) and ZPI (10 nM) were incubated with increasing concentrations of PZ for 15 min. at 22° C. before remaining factor Xa activity was determined by amidolytic assay. (□), factor Xa 2.5 nM; (○), factor Xa 5.0 nM.

Figure 4C:
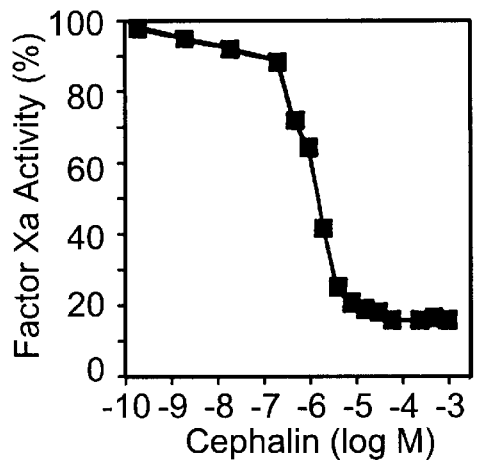

FIG. 4C shows the cephalin dose/response. Reactions containing factor Xa (2.5 nM), CaCl$_2$ (4 mM), PZ 40 nM), and ZPI 10 nM) were incubated with increasing concentrations of cephalin for 15 min. at 22° C. before remaining factor Xa activity was determined by amidolytic assay.

Figure 4D:
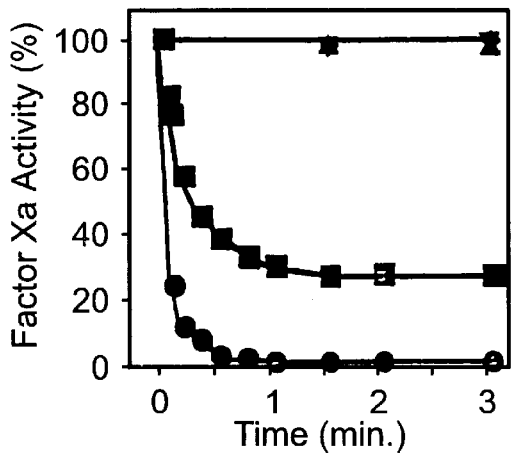

FIG. 4D shows time course of factor Xa inhibition by PZ/ZPI. Reactions containing factor Xa (5.0 nM), with or without CaCl$_2$ (4 mM), with or without cephalin (15 $\mu$M), and with or without PZ (40 nM) were incubated 5 min. at 22° C. before the addition of ZPI (10 nM). At the specified times thereafter remaining factor Xa activity was determined by bioassay or amidolytic assay. Bioassay: (●), with all reactants. Amidolytic assay: (■), with all reactants; (▼), without CaCl$_2$; (▲), without cephalin; (♦), without PZ.

Figure 5:
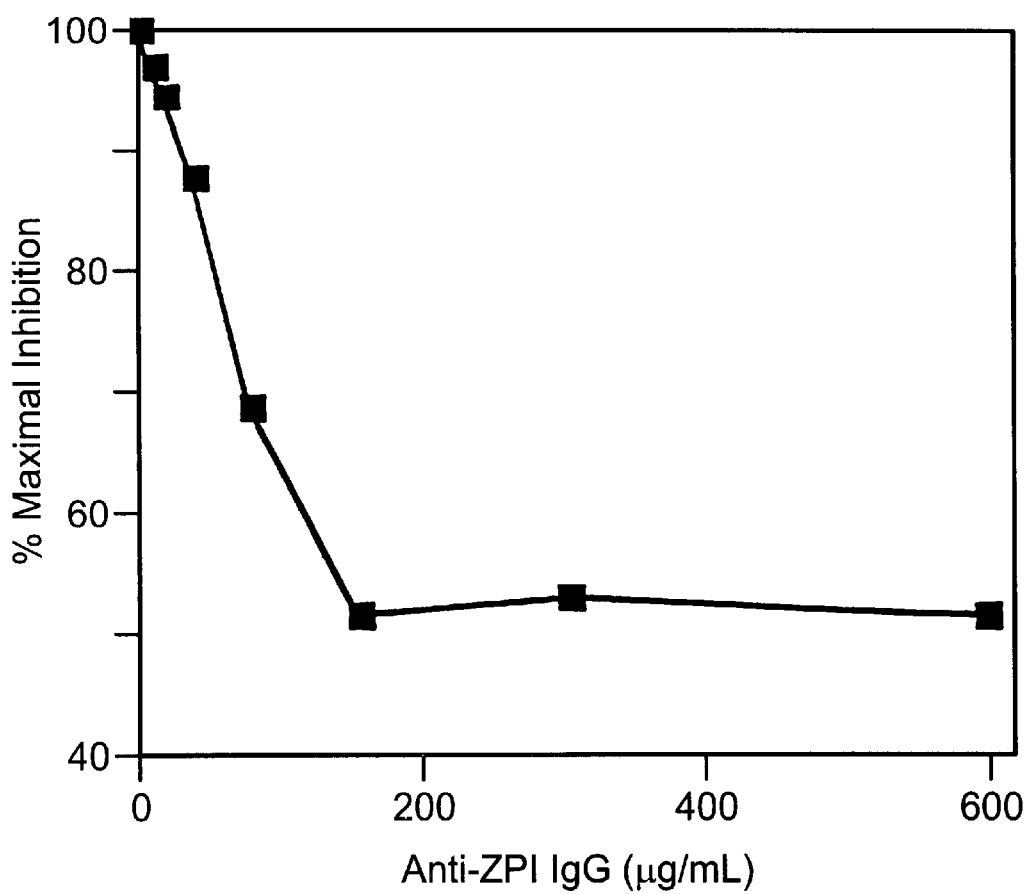

FIG. 5 is a graphical representation which shows the effect of anti-ZPI antibodies on factor Xa-induced coagulation of plasma. Reactions (200 $\mu$L) containing factor Xa (0.125 nM), CaCl$_2$ (5 mM), cephalin (18.75 $\mu$M), with or without PZ (50 nM) were incubated in the sample cup of a fibrometer. After 2 min. at 37° C., 50 $\mu$L) of factor X deficient plasma which had been treated with rabbit preimmune IgG (600 $\mu$g/mL) or immune anti-ZPI IgG at increasing concentrations for 30 min. was added and the clotting time measured. Apparent factor Xa inhibition (76%) produced by the inclusion of PZ during the preincubation period and using plasma treated with preimmune IgG is listed as maximal PZ-dependent inhibition (100% on the ordinate). The concentration of Anti-ZPI IgG used to treat the plasma is listed on the abscissa.

FIG. 6 shows the nucleotide sequence (SEQ ID NO: 7) and deduced amino acid sequence (SEQ ID NO: 8) of human ZPI CDNA. The amino acid sequence is shown in single letter code beneath the nucleotide sequence. Nucleotide/ amino acid numbers are shown in the column at the left. Translation is depicted as starting at ATG$_6$(nt 467). An alternative initiation codon, ATG$_5$(nt 347), is underlined in dashes (see Example II). Amino acid sequences derived from purified plasma ZPI are underlined. N* denote potential sites of N-linked glycosylation and the tyrosine residue at the putative P$_1$ site at the reactive center of ZPI is shown in bold print. The amino acid sequence is shown in three letter code in the attached Sequence Listing.

Figure 7:
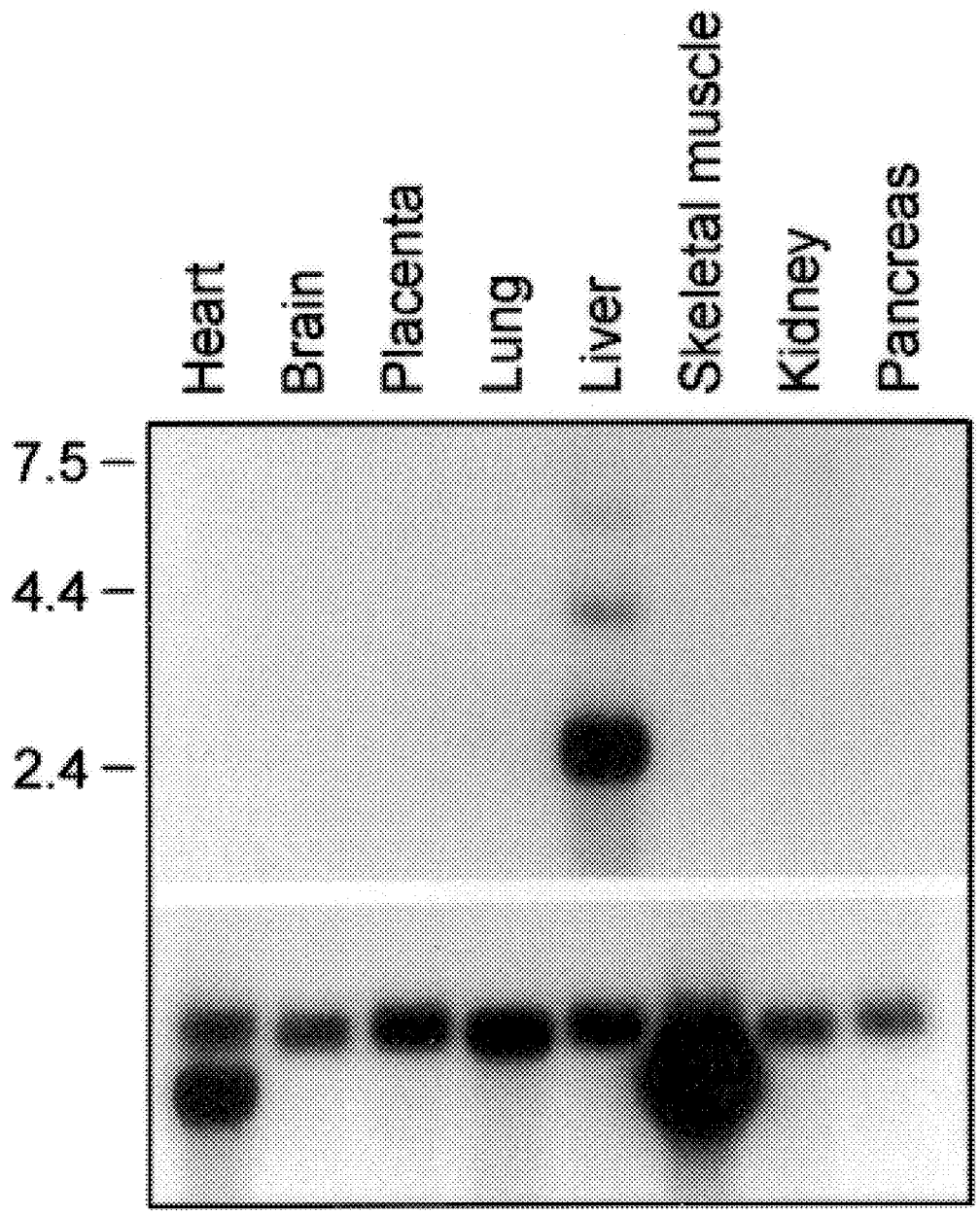

FIG. 7 shows the Northern analysis of multiple tissues for ZPX mRNA. A Northern blot nitrocellulose membrane containing 2 $\mu$g poly A$^+$ mRNA from various human tissues in each lane was hybridized with a $^{32}$P-labeled full length ZPI cDNA probe (above) or a $^{32}$P-labeled β-actin cDNA probe (below).

FIG. 8 shows the alignment of the C-terminal amino acid sequences of ZPI and other serpins. Amino acid sequences of rat rasp-1 (RASP-1) and human α$_1$-antitrypsin (A1AT), antitrypsin related sequence (A1AU), antithrombin (AT-III), heparin cofactor II (HC-II), and protease nexin 1 (PN-1) were extracted from the GenBank data base (accession numbers 2143953, 1703025, 112891, 113936, 123055, and 121110, respectively). Identical amino acids are darkly shaded. The arrowhead indicates the column containing the P$_1$ residue at the reactive center of each serpin.

Figure 9:
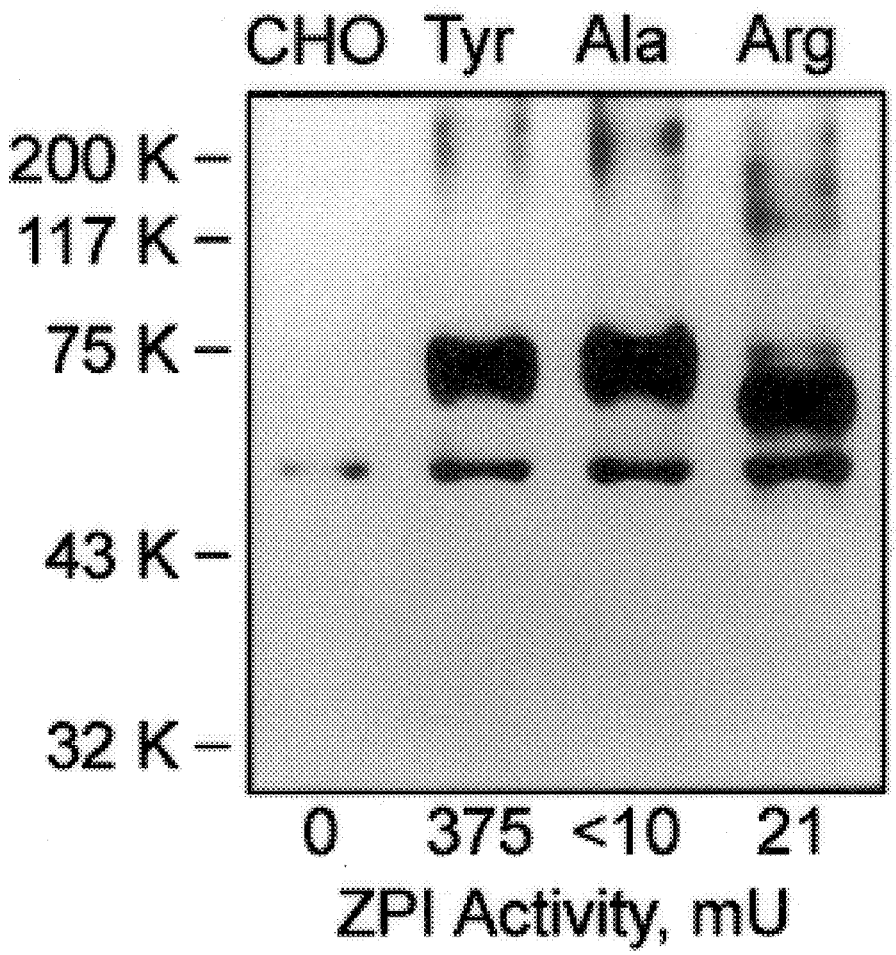

FIG. 9 shows the Western blot analysis of wild-type and altered forms of recombinant ZPI. Serum-free conditioned media (10 $\mu$L) from non-transfected CHO cells (CHO) and CHO cells expressing rZPI(WT) (Tyr), rZPI(Y387A)(Ala) and rZPI(Y387R) (Arg) were analyzed by 12% SDS-PAGE and Western blotting using a mouse monoclonal anti-ZPI antibody. The migration of pre-stained molecular weight standards listed in kDa is depicted on the left. Below the blot is listed the ZPI activity of each conditioned media (average of duplicate measurements). The protein band identified at ~54,000 is detected in the conditioned media of non-transfected CHO cells and appears to be unrelated to rZPI.

In order to illustrate the invention in greater detail, the following specific laboratory examples were carried out. Although specific examples are thus illustrated herein, it will be appreciated that the invention is not limited to these specific, illustrative examples or the details therein.

EXAMPLE I

Purification and Isolation of ZPI from Human Plasma

Materials and Methods

Materials. Sodium dodecyl sulfate (SDS), HEPES, MES, Trizma Base, Diisopropylfluorophosphate (DFP), Triton X-100, Tween 20, ethylenediaminetetraacetic acid (EDTA), polyethylene glycol (8,000 MW) S Fast Flow, bovine serum albumin, and rabbit brain cephalin were from Sigma Chemical Co. (St. Louis, Mo.). Mono-Q, Monol-S and heparin-Sepharose were purchased from Pharmacia Biotech (Piscataway, N.J.). Low molecular weight standards for polyacrylamide gel electrophoresis were from Bio-Rad Laboratories (Richmond, Calif.) and protein A-agarose from Repligen (Cambridge, Mass.). Spectrazyme Xa (MeO-CO-D-CHG-Gly-Arg-pNA.AcOH) was from American Diagnostica, Inc. (Greenwich, Conn.). Plasma/serum. Factor X deficient plasma was purchased from George King Biomedical (Overland Park, Kans.). To produce serum, fresh blood was allowed to clot for one hour at 37° C., the clot rimmed, and serum collected following centrifugation (10,000 g, 20 min). Barium-absorbed serum was produced by adding sodium oxalate (10 mM final) and two subsequent absorptions with barium sulfate (100 mg/mL, 4° C., 30 min). By monoclonal antibody sandwich immunoassay (8), the barium absorbed serum contained 0.10 μg/mL PZ.

Proteins. Alpha-1-antitrypsin was purchased from Sigma, alpha-2-antiplasmin and thrombin from American Diagnostica, Inc., protein C inhibitor (PCI) from Enzyme Research Laboratories (South Bend, Ind.), and antithrombin III from chromogenix AB (Molndal, Sweden). Alpha-2-macroglobulin was a gift from A. Schwartz (Washington University, St. Louis) and heparin cofactor II a gift from D. Tollefsen (Washington University). Inter-alpha-trypsin inhibitor was purified as previously described (12). Prothrombin and factor X were purified and factor Xa was produced from purified factor X using insolubilized X-coagulant protein from Russells viper venom as previously described (13). Additional factor Xa was purchased from Enzyme Research Laboratories.

PZ was isolated from citrated fresh frozen plasma (Missouri-Illinois Regional Red Cross) using a four step purification procedure that included barium citrate absorption-elution, ammonium sulfate fractionation, monoclonal antibody anti-PZ immunoaffinity chromatography and Mono-Q anion exchange chromatography. Thrombin-cleaved PZ ($PZ_T$) was produced by incubating 1 mg/mL PZ with 300 U/mL thrombin in 0.1 M NaCl, 0.05 M Tris-HCl, pH 8.0 for 3 hours at 37° C. The solution was treated with DFP (5 mM final) before removing the thrombin by passage through a small column of CG-50 in the same buffer (7). The N-terminal amino acid sequence of $PZ_T$ (~56,000 MW) (7) after SDS-PAGE, transfer to a PVDF-Plus membrane (Micron Separations, Inc., Westborough, Mass.) and gas-phase sequencing (Applied Biosystems, Foster City, Calif.) by the Protein Chemistry Laboratory (Washington University) is RYKGGSPXISQPXL (X=indeterminant). Using the conventional three-letter amino acid symbols required by 37 CFR §1.821–1.825, this sequence is as follows:

[SEQ ID NO:1]
Leu Ala Pro Ser Pro Gln Ser Pro Glu Xaa Xaa.
1             5            10

This amino acid sequence is identical to the sequence of PZ beginning at residue 44 of the mature protein. Thus, thrombin appears to cleave PZ following Arg43 thereby separating the Gla-domain from the remainder of the molecule.

One-stage, factor Xa-induced coagulation assay. Cephalin (75 μM) 50 μL, 50 μL $CaCl_2$ (25 mM), 50 μL PZ or $PZ_T$ (160 nM), and 50 μL factor Xa (0.5 nM) are incubated at 37° C. in the sample cup of a fibrometer (BBL, Cockeysville, Md.). After 2 minutes, 50 μL factor X deficient plasma is added and the clotting time measured. In certain tests the PZ or factor Xa were added at varying times during the preincubation period and the cephalin or PZ reagents were added to the reaction with the factor X deficient plasma (100 μL of 1:1 mixtures). Apparent factor Xa activity is determined by comparing the clotting time with a standard curve constructed using various concentrations of factor Xa in the absence of PZ.

Factor Xa bioassay. Cephalin (75 μM) 50 μL, 50 μL $CaCl_2$ (25 mM), and 50 μL buffer containing 0.1 M NaCl, 0.05 M HEPES, pH 7.4, and bovine serum albumin (1 mg/mL) (HSA) are incubated at 37° C. After 30 seconds, 50 μL of the sample diluted in HSA with 1 mM EDTA is added followed immediately by 50 μL of factor X deficient plasma. Apparent factor Xa activity is determined by comparing the clotting time with a factor Xa standard curve.

Factor Xa amidolytic assay. Mixtures (100 μL) containing various concentrations of cephalin, PZ, ZPI, factor Xa and Ca++ ions in HSA buffer are incubated at 22° C. in the wells of a microtiter plate. After the specified period of time, 50 μL of Spectrazyme Xa (0.5 mM) is added and the initial rate of substrate cleavage ($A_{405}$/min.) determined in a Vmax microtiter plate reader (Molecular Devices, Menlo Park, Calif.). In tests studying the time course of factor Xa inhibition by PZ/ZPI, the solution containing the Spectrazyme Xa (0.5 mM) also contained 15 mM EDTA and 0.3 M Tris-HCl, pH 8.3. Factor Xa activity is determined by comparing the initial rate of substrate cleavage with a standard curve produced with various concentrations of factor Xa in the same buffer conditions.

Two-stage factor Xa inhibition assay. To measure ZPI functional activity 10 μL cephalin (75 μM), 10 μL $CaCl_2$ (25 mM), 10 μL PZ (200 nM), 10 μL of the sample to be tested diluted in HSA, and 10 μL factor Xa (2.5 nM) are incubated in the sample cup of a fibrometer at 37° C. After 60 seconds, 50 μL HSA, 50 μL cephalin (75 μM), 50 ML $CaCl_2$ (25 mM) and 50 ML factor X deficient plasma are added in succession and the clotting time measured. ZPI activity is determined by comparing the clotting time with a standard curve produced using various concentrations of purified ZPI. The activity of 1 μg purified ZPI was arbitrarily assigned a value of 1 unit.

Purification of ZPI. Human citrate fresh frozen plasma (2.3 liters) from the Missouri-Illinois Regional Red Cross was thawed at 37° C. and transferred to the cold room. A six-step purification was carried out as follows:

1. Barium citrate adsorption and ammonium sulfate fractionation (4° C.). 230 mL of 1.0 M $BaCl_2$ was added dropwise over 45 minutes and the mixture was stirred an additional 15 min. The barium citrate precipitate was removed by centrifugation at 3,000 g for 20 min. and supernatant plasma collected. Ammonium sulfate was added to 45% saturation and the mixture stirred for 30 min. before the precipitate was removed by centrifugation at 10,000 g for 20 min. Sufficient ammonium sulfate was added to bring the supernatant to 75% saturation and the mixture stirred for 30 min. before centrifugation at 10,000 g for 20 min. The protein precipitate was dissolved in 0.1 M NaCl, 0.05 M Tris-HCl, pH 7.5, treated with DFP (1 mM) and dialyzed overnight against the same buffer.

2. Polyethylene glycol (PEG) fractionation (22° C.). Sufficient 50% w/v PEG (8,000 MW) was added dropwise to the sample to produce a PEG concentration of 7.5% and the mixture stirred for 30 min. before the precipitate was removed by centrifugation at 10,000 g for 20 min. PEG (50% w/v) was added dropwise to the supernatant solution to produce a PEG concentration of 18.5% and the mixture stirred for 30 min. before centrifugation at 10,000 g for 20 min. The protein precipitate was dissolved in 0.1 M NaCl, 0.020 M MES, pH 6.15 and treated with DFP (1 mM).

3. S Fast Flow cation exchange chromatography (4° C.). The sample was applied at flow rate of 150 mL/hr to a 5×47 cm. column of S Fast Flow equilibrated in 0.1 M NaCl, 0.02 M MES, pH 6.15. The column was washed with 1.5 L of the same buffer and then eluted with a linear gradient to 0.5 M NaCl, 0.02 M MES, pH 6.15 over 8 L. Fractions containing ZPI activity, which eluted at ~0.25 M NaCl, were combined and the pool concentrated to 25 mL (YM 10, Amicon, Danvers, Mass.) and treated with DFP (5 mM).

4. Mono-Q anion exchange chromatography (22° C.). The concentrated sample was diluted 2.5-fold with 0.02 M MES, pH 6.15 and applied at a flow rate of 1.5 mL/min. to a 10 mL Mono-Q column equilibrated in 0.1 M NaCl, 0.02 M MES, pH 6.15 containing 0.1% (v/v) Tween-20. The column was washed with 15 mL of the same buffer and then eluted with a linear gradient to 0.5 M NaCl in the same buffer over 100 mL. Fractions containing ZPI activity, which eluted at ~0.18 M NaCl were combined and treated with DFP (5 mM).

5. Heparin-Sepharose affinity chromatography (22° C.). The sample was diluted 2-fold with 0.02 M MES, pH 6.15 and applied at a flow rate of 1 mL/min. to a 5 mL heparin-Sepharose column equilibrated in 0.1 M NaCl, 0.02 N MES, pH 6.15 containing 0.1% (v/v) Tween-20. The column was washed with 10 mL of the same buffer and then eluted with a linear gradient to 0.6 M NaCl in the same buffer over 50 mL. Fractions containing ZPI activity, which eluted at ~0.25 M NaCl, were pooled and treated with DFP (5 mM).

6. Mono-S cation exchange chromatography (22° C.). The sample was diluted 3-fold with 0.02 M MES, pH 6.15 and applied at a flow rate of 0.5 mL/min. to a 1 mL Mono-S column equilibrated in 0.1 M NaCl, 0.02 M MES, pH 6.15 containing 0.01% (v/v) Tween-20. The column was washed with 2 mL of the same buffer and then eluted with a linear gradient to 0.5 M NaCl in the same buffer over 20 mL. Fractions containing ZPI activity, which eluted at ~0.25 M NaCl, were pooled and the purified ZPI stored at −70° C. in small aliquots. The molar concentration of ZPI was estimated assuming a ZPI concentration of 1.0 mg/mL produces an absorbance of 280 nm ($A_{280}$) of 1.0 and a molecular weight of 72,000.

The foregoing six-step purification of ZPI is summarized in Table II, below.

Other Methods. SDS polyacrylamide gel electrophoresis (SDS-PAGE) was performed using the method of Laemmli (14). Rabbit polyclonal anti-ZPI antibodies were developed as previously described using purified ZPI as immunogen (15). Pre-immune and immune IgG were isolated using protein A-agarose. N-terminal amino acid sequence analysis of purified ZPI was performed by the Protein Chemistry Laboratory (Washington University) using a gas-phase sequenator (Applied Biosystems). Two separate analyses were performed with 0.3 nmol of ZPI and gave identical results. The phospholipid content of the rabbit brain cephalin was determined as inorganic phosphate (16).

Results

Figure 1:
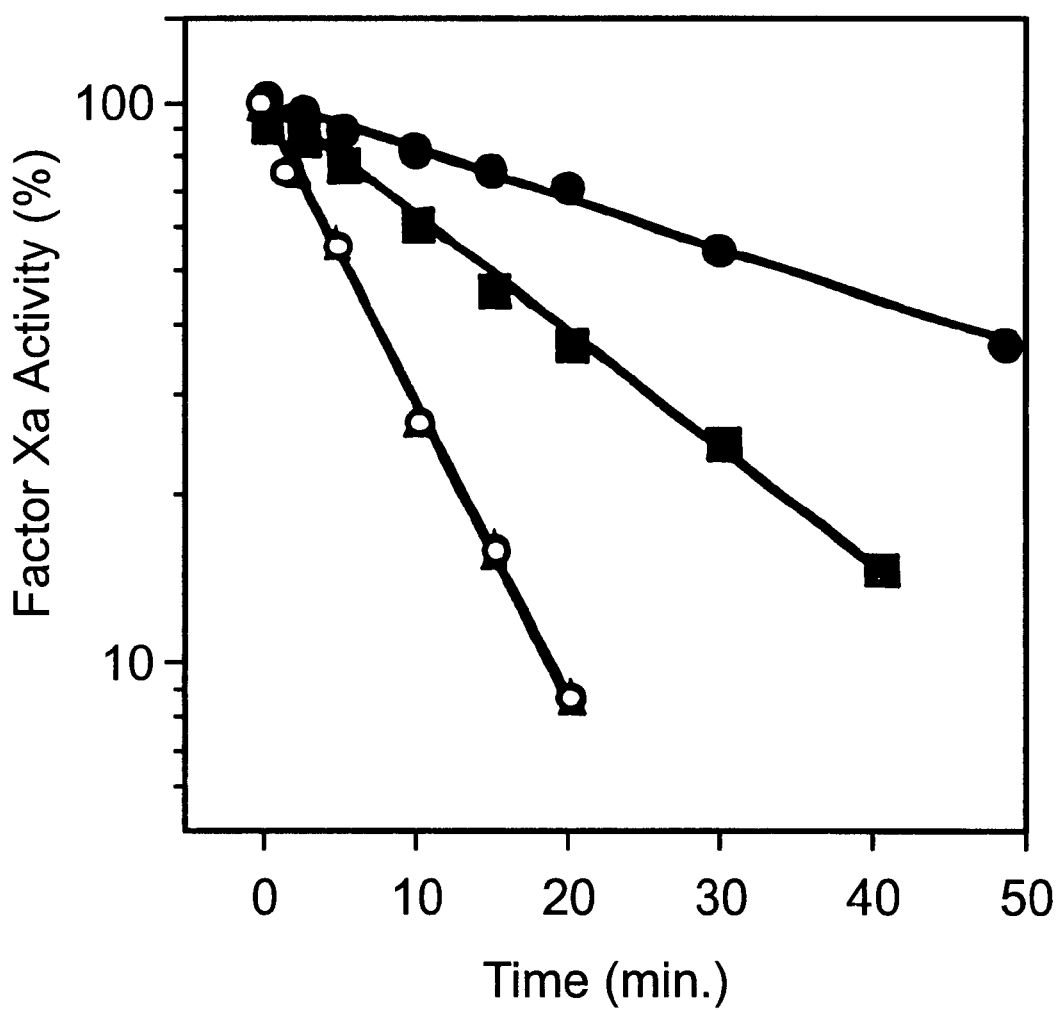
FIG. 1 is a graphical representation which shows the effect of PZ on the inhibition of factor Xa by antithrombin III. Reactions containing factor Xa (5 nM), CaCl$_2$ (4 mM), with or without PZ (40 nM), and with or without cephalin (15 $\mu$M) were incubated 5 min. at 22° C. before the addition of antithrombin III (3.4 $\mu$M). At the indicated times thereafter, samples were removed, diluted in HSA with 1 mM EDTA, and assayed for factor Xa activity by bioassay.

Reduction in Factor Xa procoagulant activity in the presence of PZ, Ca++ ions and phospholipids Initial studies investigating the potential function of human PZ showed that the apparent procoagulant activity of factor Xa in a one-stage plasma coagulation assay was reduced if the factor Xa was first incubated with PZ (Table I). The inhibitory effect was time dependent, required the presence of calcium ions and procoagulant phospholipids (rabbit brain cephalin), and appeared predominantly related to the period of preincubation of PZ with phospholipids (Table I). Thrombin treatment of PZ, which cleaves PZ at Arg43 and separates the Gla domain from the remainder of the molecule (see Methods), abolished the inhibitory effect. These results suggest that an interaction between factor Xa and PZ may occur at the phospholipid surface. Consistent with this belief, the rate of inhibition of factor Xa by antithrombin III was slowed by PZ in the presence of cephalin and Ca++ ions (t½35 min. vs. 15 min.) (FIG. 1).

To further evaluate the effect of PZ on factor Xa inactivation, the time course of the loss of factor Xa activity in PZ-depleted serum with and without added PZ in the presence of cephalin and $CaCl_2$ was determined by bioassay (FIG. 2). An additional early loss of factor Xa activity is demonstrable in the presence of PZ suggesting that serum contains a PZ-dependent factor Xa inhibitor(s). However, the curves describing the loss of factor Xa activity in serum in the presence and absence of PZ intersect so that ultimately the factor Xa activity remaining in serum with PZ is greater than that in serum without PZ. In systems containing purified proteins, PZ does not enhance the inhibition of factor Xa by alpha-1-antitrypsin, protein C inhibitor, alpha-2-antiplasmin, heparin cofactor II, inter-alpha-trypsin inhibitor or alpha-2-macroglobulin.

Isolation of ZPI

A two-stage bioassay designed to measure PZ-dependent factor Xa inhibition was used to isolate a PZ-dependent protease inhibitor (ZPI) from plasma (Methods, Table II). The ZPI activity of the starting plasma could not be measured due to thrombin generation and fibrin formation during the first stage of the two-stage factor Xa inhibition assay. Nevertheless, assuming a 50%–75% recovery of ZPI following ammonium sulfate fractionation of plasma (Table II), it is estimated that the plasma concentration of ZPI is 1.0–1.6 µg/mL (14–22 nM).

By SDS-PAGE analysis, ZPI migrates as a single chain protein with an apparent molecular weight of 72 kDa (FIG. 3). Preliminary characterization of the purified protein shows that ZPI activity is abolished by treatment with SDS (1%), urea (8 M), and 2-mercaptoethanol (5% v/v), but is stable in Tween-20 (2%) and Triton X-100 (2%). ZPI is also unaffected by methylamine treatment under conditions that completely inactivate alpha-2-macroglobulin. The N-terminal amino acid sequence of ZPI is LAPSPQSPEXXA (X=indeterminant), SEQ ID NO: 1. This sequence does not match nor show significant homology with the sequences accessible in publicly available protein or DNA data bases. Thus, ZPI may represent a previously unidentified gene-product.

PZ-Dependent Inhibition of Factor Xa by ZPI

To further investigate the factor Xa-ZPI interaction, mixtures containing factor Xa, $CaCl_2$, cephalin and PZ were incubated with increasing concentrations of ZPI for 15 minutes (22° C.) (FIG. 4A). The remaining factor Xa activity was then determined in an amidolytic assay (Methods) following the addition of Spectrazyme Xa. The results suggest a high affinity interaction between ZPI and factor Xa with a stoichiometry of 1.2:1 (ZPI:factor Xa). Even at relatively high concentrations of ZPI, however, a significant amount (~20%) of factor Xa amidolytic activity persists.

The PZ-dose/response of ZPI-mediated factor Xa inhibition was evaluated in similar reactions (FIG. 4B). Again an apparent stoichiometric relationship between PZ and factor Xa was demonstrated with a molar ratio of 1.4:1 (PZ:factor Xa). Optimal PZ-dependent inhibition of factor Xa by ZPI occurs at concentration of mixed rabbit brain phospholipids (cephalin) of ≧15 µM (FIG. 4C). The inhibition of factor Xa produced by ZPI is rapid following the incubation of factor Xa with PZ, Ca++ ions and cephalin (FIG. 4D). Maximal factor Xa inhibition as assessed by amidolytic assay (70%) and bioassay (97%) is reached within <1 minute. Using the amidolytic assay (FIG. 3D) or bioassay, no factor Xa inhibition occurs if PZ, phospholipids, or Ca++ ions (1 mM EDTA) is omitted from the reactions.

Serum and plasma were treated with rabbit polyclonal anti-ZPI antibodies to determine the contribution of serum ZPI to the early, enhanced inhibition of factor Xa produced in the presence of PZ and the contribution of plasma ZPI to the apparent reduction in factor Xa activity produced by its incubation with PZ, phospholipids and Ca++ ions prior to the one-stage bioassay. Treatment with anti-ZPI antibodies completely abrogated the PZ-dependent factor Xa inhibition in serum (FIG. 2), but reduced the PZ-mediated inhibitory effect in the plasma one-stage bioassay by only ~50% (FIG. 5).

Despite its isolation several years ago, the physiologic function of PZ heretofore has remained uncertain. The results in Example I show that PZ slows the inhibition of factor Xa by antithrombin III in the presence of phospholipids and Ca++ ions, but also plays an important role in the inhibition of factor Xa by a novel plasma protein that is herein termed protein Z-dependent protease inhibitor, ZPI. PZ and/or its apparent interaction with factor Xa, however, may serve other functions. In this regard, it is important to note that inhibition of ZPI in the substrate plasma of the one-stage coagulation assay reduced the apparent inhibitory effect of the preincubation of PZ with phospholipids, Ca++ ions, and factor Xa by only ~50%.

The remaining PZ-mediated inhibitory effect could be related to its interference with the binding of other proteins to phospholipids (e.g. prothrombin), the slow dissociation of factor Xa from a putative factor Xa-PZ-phospholipid-Ca++ complex, or the presence of additional PZ-dependent coagulation inhibitors in plasma. The relatively slow association of PZ with phospholipids (11) is consistent with the time-dependent inhibitory effect of PZ during its incubation with phospholipids and Ca++ ions in the one-stage assay and, moreover, presumably also explains the absence of clotting time prolongation when PZ is added instead with the substrate plasma to the reaction.

The inhibition of factor Xa by presumed physiologic concentrations of ZPI requires the presence of phospholipids, Ca++ ions and PZ and appears to involve a stoichiometric complex of factor Xa, PZ and ZPI at the phospholipid surface. The apparent inhibition of factor Xa produced by ZPI, however, is considerably less when remaining factor Xa activity is measured using a small molecular weight chromogenic substrate (Spectrazyme Xa), than when remaining factor Xa activity is measured by bioassay. The cause of this discrepancy is not clear.

One explanation of the discrepancy could be the presence in the factor Xa preparations of degraded forms of factor Xa that retain activity against the chromogenic substrate but do not bind phospholipid and thus are not inhibited by ZPI and lack procoagulant activity. The disparity between the inhibitory effect measured by amidolytic assay and bioassay, however, was consistently seen with several factor Xa preparations whose amidolytic activity was bound by barium sulfate (>97%) and which by SDS-PAGE analysis contained a spectrum of ratios of α and 62 forms of factor Xa (α:β=1:1 to 1:4) and <5% additionally degraded factor Xa. Moreover, the chromogenic activity of the factor Xa preparations was inhibited >99% by tissue factor pathway inhibitor (TFPI), suggesting that the residual chromogenic activity remaining following the interaction of factor Xa with ZPI was not due to a contaminating protease.

EXAMPLE II

Isolation and Cloning of ZPI cDNA

Material and Methods

Materials: Fresh frozen human plasma was purchased from the Regional Red Cross (St. Louis, Mo.). Multiple human tissue RNA blot and human adult live CDNA library were from Clontech (Palo Alto, Calif.); human fetal liver cDNA library was from Strategene (La Jolla, Calif.); nitrocellulose membrane from Schleicher & Schuell, Inc. (Keene, N.H.); PVDF membrane from Micron Separations, Inc. (Westborough, Mass.); $^{32}$P-α dATP from NEN Life Scientific, Inc. (Boston, Mass.); and dNTPs from Pharmacia Biotech, Inc. (Piscataway, N.J.). Taq DNA polymerase, DMEM culture medium, fetal calf serum and LipofectAMINE were from Gibco BRL, Life Technologies (Gaithersburg, Md.). Antibiotic G418 (Geneticin) was purchased from Mediatech, Inc. (Herndon, Va.). Chinese hamster ovary (CHO) cells were from the ATCC (Manassas, Va.). ITS+3 media supplement, protease inhibitor cocktail, soybean trypsin inhibitor, aprotinin, and rabbit brain cephalin were from Sigma Chemical (St. Louis, Mo.). Factor X deficient plasma was from George King Biomedical, Inc. (Overland Park, Kans.). Prestained molecular weight standards for sodium dodecyl sulfate-polyacrylamide gel electrophoresis (SDS-PAGE) were purchased from Bio-Rad (Hercules, Calif.).

Proteins: PZ and ZPI were purified from human plasma as previously described (17). A mouse monoclonal anti-ZPI antibody (MC4249.2) was produced using established and previously reported techniques (18).

N-terminal amino acid sequencing of ZPI and trypsin-treated ZPI: Samples containing 20 μg ZPI or 20 μg ZPI that had been digested with trypsin (1:200 w/w) for 30 minutes at 22° C. were reduced with 2-mercaptoethanol (5%) and separated by 12% SDS-PAGE and electro-transferred to a PVDF membrane. The membrane was stained for 10 minutes with 0.025% Coomassie Brilliant Blue R-250 in 10% methanol/7% acetic acid, washed with distilled water and allowed to air dry. Discernible protein bands of apparent molecular weight 72,000 for ZPI and 43,000 and 41,000 for trypsin-treated ZPI were cut from the membrane and sequenced by the Protein Chemistry Laboratory (Washington University, St. Louis, Mo.).

ZPI cDNA cloning: The N-terminal amino acid sequence of the two tryptic peptides derived from ZPI was highly homologous to the amino acid sequence predicted by the previously reported cDNA for rat regeneration-associated serpin (rasp-1, GeneBank Accession No. 2143953 (see Results) (19). Nucleotide sequences derived from rasp-1 cDNA, 496–518 (ACCCAGGGTA GCTTTGCCTT CAT), SEQ ID NO: 3, and

805–825(GTACATCATG GGCACCTTAA C), SEQ ID NO: 4, were used as the basis for 5'- and 3'-primers, respectively, in a PCR reaction to amplify a DNA fragment from a human fetal liver cDNA library (Strategene). The PCR product, ~330 bp, was cloned into PGEM-T Easy (Promega, Madison, Wis.) and was found to be 80% homologous with rasp-1 cDNA by sequence analysis. Following radiolabeling with $^{32}$P-α dATP and random priming, the PCR product was used as a probe to screen approximately 2×10$^6$ plaque-forming units from a human liver cDNA library (Clontech). Hybridization was performed at 42° C. in 5×SSPE, 5×Denhardt's solution, 1% SDS, 50% formamide, and 100 μg/mL denatured salmon sperm. Filters were washed with 1×SSC and 0.1% SDS solution at room temperature for 15 minutes and then washed three times with the same solution at 65° C. for 30 minutes. The twenty-one positive clones that remained after plaque purification contained cDNAs of four different lengths. A representative of the longest cDNA was sequenced in its entirety in both directions.

Northern blot analysis: $^{32}$P-labeled full length ZPI cDNA was used as a probe for analysis of a human multiple tissue Northern blot membrane from Clontech (Palo Alto, Calif.) containing 2 μg poly A+ RNA per sample. Hybridization was performed under the stringent conditions suggested by the manufacturer; autoradiography was allowed to proceed overnight.

In vitro expression of wild-type and altered forms of recombinant ZPI (rZPI): A 2.2 fragment of the ZPI CDNA was produced by treatment with Sac 1 and Hind III and inserted into the multiple cloning site of pBluescript KS II. This fragment contained part of the 5' untranslated region, the entire open reading frame, and the 33 untranslated region of the ZPI cDNA. A 2.3 kb fragment of pBluescript-ZPI was released by Pvu II treatment and inserted by blunt-end ligation into the EcoR V site of the expression vector pCMV (20) producing pCMV-ZPI(WT). This 2.3 kb DNA fragment contained: 1) ZPI CDNA beginning 120 bp upstream of $ATG_6$ and lacking the remainder of the 5' untranslated ZPI cDNA including $ATG_1$–$ATG_5$; 2) the coding and 3' untranslated regions of ZPI cDNA; and 3) ~200 bp of pBluescript KS II DNA. In pCMV, expression is driven by the cytomegalovirus early promoter/enhancer.

PCR-based site-directed mutagenesis with pCMV-ZPI (WT) as template was used to change the codon for Y387 (TAT) in ZPI to that for alanine (GCT) or arginine (CGT). Mutations were confirmed by sequencing the ZPI cDNA between Nsi I (nt 1544) and Spe I (nt 1944) restriction sites which are upstream and downstream of the mutation site. These fragments were then inserted in pCMV-ZPI(WT) at Nsi I–Spe I to produce pCMV-ZPI(Y387A) and pCMV-ZPI (Y387R). pCMV-ZPI(WT), pCMV-ZPI(Y387A) and pCMV-ZPI(Y387R) were co-transfected with pSV2neo into CHO cells using LipofectAMINE (GIBCO BRL) according to the manufacturer's instructions. Cell clones resistant to G418 were picked at three weeks and expanded. Non-transfected CHO cells and stable CHO clones expressing rZPI(WT), rZPI(Y387A), and rZPI(Y387R) were cultured in 5% $CO_2$ with DMEM and 10% fetal calf serum in six well culture plates (Costar, Corning, Inc., Corning, N.Y.). After the cells reached confluence, the media was removed and the cells were washed three times with 5 mL of DMEM before 1 ml of serum-free media consisting of DMEM with ITS+3 media supplement (insulin, transferring, selenium, Sigma) was added to each well. After an additional 48 hrs. of culture, the conditioned media was collected, centrifuged (14,000×g×30 sec.) to remove cell debris, and analyzed by Western blotting and ZPI functional assay. In some experiments, aprotinin (1 μg/mL) and soybean trypsin inhibitor (2.5 μg/mL) were included in the serum-free media and a 1:10 dilution of protease inhibitor cocktail (Sigma) containing 4-(2-aminoethyl)benzenesulfonyl fluoride (AEBSF)(100 mM), pepstatin A (1.5 mM), trans-expoxysucciniyl-L-leucyl-amido(4-guanidino)butane (E-64)(1.4 mM), bestatin (4 mM), leupeptin (2.2 mM), and aprotinin (80 μM) was added to the conditioned media at the time of its collection.

ZPI functional assay: A two-stage factor Xa inhibition assay was used to measure ZPI functional activity as previously described (17). Twenty μL rabbit brain cephalin (75 μM), 20 μL $CaCl_2$ (25 nM), 20 μL PZ (200 nM) or 20 μL HSA (0.1 M NaCl, 0.05 M Hepes, pH 7.4, with 1 mg/mL bovine serum albumin), 20 μL of the sample to be tested, and 20 μL factor Xa (1 nM) were incubated in the sample cup of a fibrometer at 37° C. After 60 sec., 50 μL cephalin (75 μM), 50 μL $CaCl_2$(25 mM), and 50 μL factor X-deficient plasma were added in succession and the clotting time measured. ZPI activity was determined by comparing the clotting time with a standard curve produced by using various concentrations of purified ZPI derived from plasma. One μg of purified plasma ZPI was defined to possess 1000 milliunits (mU) of activity.

Western Blotting: SDS-polyacrylamide gel electrophoresis, the electro-transfer of proteins to nitrocellulose, and incubation of the blot with the monoclonal anti-ZPI antibody (MC4249.2) (10 μg/mL) were performed using previously described methods (21). Antibody binding to the blot was detected using horseradish peroxidase-labeled goat anti-mouse IgG antibodies (Sigma) and enhanced chemoluminescence (ECL) with Super Signal substrate (Pierce, Rockford, Ill.).

Results

Isolation and Sequence of ZPI cDNA

In a search of publicly available protein and DNA databases, the N-terminal acid sequence of ZPI isolated from human plasma, LAPSPQSPEXXA (X-indeterminate), SEQ ID NO: 1, did not show significant sequence homology with previously reported gene products. However, the N-terminal sequence of peptides of 43 kDa and 41 kDa produced by trypsin treatment of ZPI were the same, NLELGLTQSFAFIHKDFDV, SEQ ID NO: 5, and showed 75% identity (16 of 20 residues) with an amino acid sequence predicted by the previously reported rat regeneration-associated serpin-1 (rasp-1) cDNA (19). Oligonucleotide primers based on rasp-i cDNA sequence were used as PCR primers and a human fetal liver cDNA library (Stratagene) was used as a template to produce a ~330 bp probe for the subsequent isolation of ZPI cDNA (see Methods). Twenty-one positive plaques containing inserts of four different sizes were isolated from a human liver cDNA library (Clontech). The nucleotide sequence, SEQ ID NO: 7, and predicted amino acid sequence, SEQ ID NO: 8 of the longest ZPI cDNA insert, is shown in FIG. 6. Restriction mapping and limited sequence analysis of clones representative of the three shorter ZPI cDNA insert sizes suggest they are 5' truncated forms of the cDNA shown.

The 5' portion of the 2.44 kb ZPI cDNA contains six potential ATG translation start sites at nucleotides 156, 243, 259, 312, 347, and 467. The open reading frames following the first four ATG's encode 11, 22, 3, and 52 amino acids, respectively, before encountering stop codons. $ATG_5$ (underlined with dashes in FIG. 6) is in the same reading frame as $ATG_6$ and translation initiation at ATG, would add the forty amino acid sequence MSRSTQELLGY HCRLQDKLQEQEGSLAAEGRHSLASAADH, SEQ ID NO: 6, to the encoded protein.

Flanking nucleotides about the ATG codons, including $ATG_5$ and $ATG_6$, produce sequences that are not optimal for the initiation of translation (22). Nevertheless, $ATG_6$ is depicted as the initiator codon in FIG. 6 because additional tests (see below) showed it was sufficient for ZPI expression. On Northern analysis of a human multiple tissue blot, ~2.4 kb ZPI mRNA was strongly detected in liver, but undetectable in heart, lung, brain, spleen, testes and kidney (FIG. 7), suggesting that the liver is a major source of ZPI in vivo.

As depicted, the ZPI cDNA contains a 1335 bp open reading frame encoding a deduced protein of 444 amino acids. The predicted amino acid sequence has a typical 21 residue signal peptide that is followed by the N-terminal sequence of the purified ZPI protein. Five potential N-linked glycosylation sites are present. The nucleotide and predicted amino acid sequence of human ZPI are respectively 75% and 78% identical with those of rat rasp-1, suggesting that ZPI represents the human homologue of this rat protein.

The ZPI amino acid sequence is also 25–35% homologous with other members of the serpin superfamily of protease inhibitors, including $\alpha_1$-antitrypsin, antithrombin, heparin cofactor II and protease nexin-1. The C-terminal region of ZPI shows the greatest similarity with the other members of the serpin superfamily, whereas the sequence of the N-terminal region of ZPI, which contains a very acidic domain (residues 26–43, FIG. 6), does not show significant homology with these other serpins.

The C-terminal amino acid sequences of ZPI, rasp-1, and certain other serpins are shown in FIG. 8. Based on this alignment, the putative $P_1$ residue at the reactive centers of human ZPI and rat rasp-1 is a tyrosine. Antitrypsin-related sequence (A1AU), an apparently non-transcribed DNA sequence highly homologous to that of antitrypsin and physically linked to the antitrypsin gene, also contains an aromatic residue (tryptophan) at the $P_1$ site (23,24). In common with many other serpins, the $P_1'$ residue in ZPI is a serine, whereas the $P_1'$ residue in rasp-1 is a cysteine.

Expression of Recombinant ZPI

To confirm that the protein encoded by the isolated cDNA possesses ZPI activity and to determine the importance of Y387 to ZPI function, rZPI(WT) and two altered forms of ZPI, rZPI(Y387A) and rZPI(Y387R), were expressed in Chine hamster ovary (CHO) cells. Western blot analysis of the respective serum-free conditioned medias showed that wild type and the altered forms of rZPI were present at similar concentrations (FIG. 9). However, while rZPI(WT) and rZPI(Y387A) migrated with the same apparent molecular mass as plasma-derived ZPI (72,000 Da), the bulk of rZPI(Y387R) migrated with a molecular mass of 68,000 Da. Attempts to reduce the apparent proteolytic degradation of rZPI(Y387R) by including aprotinin and soybean trypsin inhibitor in the serum-free culture media and adding a protease inhibitor cocktail to the collected conditioned media were unsuccessful (see Methods).

In a two-stage assay of PZ-dependent factor Xa inhibition, the serum-free conditioned media containing rZPI(WT) possessed substantial ZPI activity (375 mU/mL), whereas conditioned media containing rZPI(Y387A) lacked activity (<10 mU/mL) and conditioned media containing rZPI(387R) had markedly reduced activity (21 mU/mL) (FIG. 9).

Based on oligonucleotide and amino acid sequence homology, ZPI appears to be the human counterpart of rat rasp-1. Rasp-1 was initially identified as a gene whose transcription is increased 3- to 4-fold following subtotal hepatectomy in rats (19). However, rasp-i expression is increased to a similar extent in sham-operated rats, suggesting that rasp-1 may be involved in the acute phase response. The rasp-1 gene product circulates in rat plasma with a reported molecular mass of ~50,000, whereas the molecular mass of plasma ZPI is ~72,000 (17,19). This apparent difference in the molecular size between the rat and human gene-products could be related to the extent of glycosylation. Constitutive expression of both rasp-1 (19) and ZPI genes is high in the liver and not detectable in brain, heart, lung, kidney, spleen, and testes by Northern analysis.

The ZPI cDNA is 2.44 kb in length and consistent with the smallest hybridizing species of ~2.4 kb noted in liver on Northern analysis (FIG. 7). Hybridizing bands of greater size likely represent incompletely processed forms of ZPI mRNA. The 5' region of the ZPI cDNA is relatively long (466 bp) and contains several potential ATG translation start codons. Four of these putative start codons are followed by termination codons, but the fifth ATG at nucleotide 347 is inframe with the ATG at nucleotide 467 that is tentatively designated as the authentic start codon. All these potential ATG initiation start sites are flanked by less than ideal nucleotide sequences (22). The long 5' untranslated region, the presence of multiple upstream AUG codons that encode small open reading frames, and the lack of an optimal initiation sequence could all serve to suppress ZPI mRNA translation (22,25,26). Whether this is true, and whether an alternative form of ZPI is produced through translation initiation at the fifth AUG (nt 347), will require direct testing.

ZPI has 25–35% overall homology with other members of the serpin superfamily and its primary structure contains 40 of the 5' residues previously designated as essential for serpin tertiary structure (27). These conserved residues reside in the apolar core and the spine of serpin molecules. Amino acid alignment of ZPI and rasp-1 with other serpins suggests that the $P_1$ residue at their reactive centers is a tyrosine, which would set them apart from other serpins.

To confirm the role of Y387 in the inhibition of factor Xa by ZPI, altered forms of ZPI in which this residue was changed to an alanine or arginine were evaluated. rZPI (Y387A) was stable under the tissue culture conditions required for its expression and lacked PZ-dependent antifactor Xa activity. In contrast to rZPI(WT), rZPI(Y387R) was apparently proteolytically degraded during the production of conditioned media despite the use of multiple protease inhibitors. The proteolytic event reduces the mass of ZPI by ~4,000 Da consistent with cleavage occurring following R387, but the enzyme(s) responsible for this proteolysis is not known.

In sum, the tests with rZPI(Y387A) and rZPI(Y387R) suggest that Y387 is critical for PZ-dependent factor Xa inhibition and are consistent with the notion that Y387 is the $P_1$ residue at the reactive center of ZPI.

The coagulation inhibitors PZ, ZPI and combination of PZ and ZPI can be administered to a patient by conventional means, preferably in formulations with pharmaceutically acceptable diluents and carriers. The amount of the active component in the formulation which is an administered must be an effective amount, i.e., an amount which is sufficient to inhibit coagulation. Parenteral administration of the active component such as in physiologic saline, buffered saline, e.g. phosphate-buffered saline (PBS), HEPES buffer and the like buffers, are illustrative. Other suitable formulations of the active component in pharmaceutically acceptable diluents and carriers in therapeutic dosage form can be prepared by reference to numerous general texts in the field well-known to the person skilled in the art, e.g., *Remington's Pharmaceutical Sciences*, Ed. Arthur Osol, 16th ed. 1980, Mack Publishing Co., Easton, Pa., and 18th ed. 1990.

Various other examples will be apparent to the person skilled in the art after reading the present disclosure without departing from the spirit and scope of the invention. It is intended that all such other examples be included within the scope of the appended claims.

TABLE I

Apparent inhibition of factor Xa produced by incubation with PZ, cephalin and calcium ions before one-stage assay. $PZ_T$ refers to thrombin-treated PZ (see Methods).

| Incubation Period (sec.) | | Apparent |
|---|---|---|
| Factor Xa | PZ | Inhibition (%) |
| 120 | 0 | 0 |
| 120 | 15 | 50 |
| 120 | 30 | 61 |
| 120 | 60 | 72 |
| 120 | 90 | 76 |
| 120 | 120 | 78 |
| 120 | $PZ_T$ 120 | 0 |
| 15 | 120 | 70 |
| 30 | 120 | 71 |
| 60 | 120 | 73 |
| 90 | 120 | 76 |
| 120 | 120 | 78 |
| 120 | 120 w/o cephalin | 0 |
| 120 | 120 w/o Ca++ | 0 |

TABLE II

ZPI PURIFICATION

| Step | Volume mL | Protein mg* | Activity units+ | Specific Act. units/mg | Purification-fold | Yield % |
|---|---|---|---|---|---|---|
| Plasma | 2300 | 144,740 | —# | — | — | — |
| Barium Absorption, NH₄SO₄ fractionation | 1430 | 59,730 | 1820 | 0.031 | 1.0 | 100 |
| PEG fractionation | 257 | 25,950 | 1720 | 0.066 | 2.2 | 94 |
| S-Fast Flow, Concentration | 25 | 191 | 1365 | 7.15 | 231 | 75 |
| Mono-Q | 10 | 50.2 | 1056 | 21.0 | 677 | 58 |
| Heparin-Sepharose | 5.8 | 1.32 | 837 | 634 | 20,450 | 46 |
| Mono-S | 1.9 | 0.59 | 590 | 1000 | 32,800 | 32 |

*Protein determined assuming $A_{280}$ 1.0 = 1.0 mg/mL
+Activity expressed in abitrary units with 1.0 unit = 1 ug purified ZPI
Activity of plasma could not be determined due to thrombin generation in first stage of functional assay

REFERENCES

1. Stenflo, J. Fernlund, P., Egan, W. Roepstorff, P. (1974) *Proc. Natl. Acad. Sci. USA* 71, 2730–2733.
2. Nelestuer, G. L., Zytkovicz, T. H. & Howard, J. B. (1974) *J. Biol. Chem.* 249, 6347–6350.
3. Esmon, C. T., Suttie, J. W. & Jackson, C. M. (1975) *J. Biol. Chem.* 250d, 4094–4099.
4. Prowse, C. V. & Esnouf, M. P. (1977) *Biochem. Soc. Trans.* 5, 255–256.
5. Mattock, P. & Esnouf, M. P. (1973) *Nat. New Biol.* 242, 90–92.
6. Petersen, T. E., Thogerson, H. C., Sottrup-Jensen, L., Magnusson, S. & Jornvall, H. (1980) *FEBS Lett.* 114, 278–282.
7. Broze, Jr., G. J. & Miletich, J. P. (1984) *J. Clin. Invest.* 73, 933–938.
8. Miletich, J. P. & Broze, Jr., G. J. (1987) *Blood* 69, 1580–1586.
9. Sejima, H., Hayashi, T., Deyashiki, Y., Nishioka, J. & Suzuki, K. (1990) *Biochem Biophys. Res. Com.* 171, 661–668.
10. Ichinose, A., Takeya, B., Espling, E., Iwanaga, S., Kisiel, W. & Davie, E. W. (1990) *Biochem. Biophys. Res. Commun.* 172, 1139–1144.
11. McDonald, J. F., Shah, A. M., Schwalbe, R. A., Kisiel, W., Dahlback, B. & Nelsestuen, G. L. (1997) *Biochemistry* 36, 5120–5127.
12. Pratt, C. W. & Pizzo, S. V. (1987) *Biochemistry* 26, 2855–2863.
13. Broze, Jr., G. J. Warren, L. A., Novotny, W. F., Higuchi, D. A., Girard, J. J. & Miletich, J. P. (1988) *Blood* 71, 335–343.
14. Laemmlie, M. K. (970) *Nature* 227, 680–685.
15. Vaitukaitis, J. L. (1981) *Methods Enzymol.* 73, 46–52.
16. Ames, B. W. & Dubin, D. T. (1960) *J. Biol. Chem.* 235, 769–775.
17. Han, X., Fiehler, R., and Broze, G. J., Jr. (1998) *Proc. Natl. Acad. Sci. USA* 95:9250–9255.
18. Miletich, J. P. and Broze, G. J., Jr. (1987) *Blood* 69:580–1586.
19. New, L., Liu, K., Kamali, V., Plowman, G., Naughton, B. A., and Purchio, A. F. (1996) Biochchem. Biophys. Res. Commun. 223:404–412.
20. Smith, P. L., Skelton, T. P., Fiete, D., Dharnesh, S. M., Beranek, M. C., MacPhail, L., Broze, G. J., Jr. and Baenziger, J. U. (1992) *J. Biol. Chem.* 267: 19140–19146.
21. Broze, G. J., Jr. and Miletich, J. P. (1985) *J. Clin. invest.* 76:937–946.
22. Kozak, M. (1986) *Cell* 44:283–292.
23. Kelsay, G. D., Parkar, M., and Povey, S. (1988) *Ann. Hum. Genet.* 52:151–160.
24. Bao, J.-J., Reed-Fourquet, L., Sifers, R. N., Kidd, V. J., and Woo, S. L. (1988) *Genomics* 2:165–173.
25. Phelps, D. E., zhsiao, K.-M., Li, Y., Hu, N., Franklin, D. S., Westphal, E., Lee, E. Y., and Xiong, Y. (1998) *Mol. Cell. Biol.* 18:2334–2343.
26. Stein, I., Itin, A., Einat, P., Skaliter, R., Grossman, Z., and Keshet, 3. (1998) *Mol Cell. Biol.* 18:3112–3119.
27. Huber, R., and Carrell, R. W. (1989) *Biochemistry* 28:8951–8966.

What is claimed is:

1. A method of inhibiting factor Xa in serum or plasma comprising contacting said serum or plasma with an effective inhibitory amount of the human protein Z-dependent protease inhibitor ZPI characterized as:
   (a) having a molecular weight of about 72 kDa,
   (b) being a single chain Protein with an N-terminal amino acid sequence of

[SEQ ID NO:1]
   ```
   Leu Ala Pro Ser Pro Gln Ser Pro Glu Xaa Xaa.
   1               5                   10
   ```

(c) producing greater than 95% inhibition of factor Xa in the presence of protein Z, calcium ions and cephalin.

2. A method of inhibiting factor Xa in serum or plasma comprising contacting said serum or plasma with an effective inhibitory amount of the purified and isolated human protein Z-dependent protease inhibitor having an amino acid sequence corresponding to residues 1–423 of SEQ ID NO: 8.

* * * * *

UNITED STATES PATENT AND TRADEMARK OFFICE
CERTIFICATE OF CORRECTION

PATENT NO. : 6,265,378 B1
DATED : July 24, 2001
INVENTOR(S) : George J. Broze, Jr.

It is certified that error appears in the above-identified patent and that said Letters Patent is hereby corrected as shown below:

Column 29,
Line 63, "[SEQ ID NO:1]" should read -- [SEQ ID NO:16], and --
Lines 64-54, "Xaa Xaa" should read     -- Thr Pro Ala --
              10                          10

Signed and Sealed this

Twentieth Day of April, 2004

JON W. DUDAS
*Acting Director of the United States Patent and Trademark Office*

SEQUENCE LISTING

<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<221> NAME/KEY: Xaa=Unknown amino acid
<222> LOCATION: Xaa=Indeterminate residues 10 & 11; can be any amino acid
<223> OTHER INFORMATION: /note="synthetic construct"

<400> SEQUENCE: 1

```
Leu Ala Pro Ser Pro Gln Ser Pro Glu Xaa Xaa Ala
1               5                  10
```

<210> SEQ ID NO 2
<211> LENGTH: 14
<212> TYPE: PRT
<213> ORGANISM: Artificial Sequence
<220> FEATURE:
<221> NAME/KEY: Xaa=Unknown amino acid
<222> LOCATION: Xaa=Indeterminate residue 13; can be any amino acid
<223> OTHER INFORMATION: /note="synthetic construct"

<400> SEQUENCE: 2

```
Arg Tyr Lys Gly Gly Ser Pro Xaa Ile Ser Gln Pro Xaa Leu
1               5                  10
```

<210> SEQ ID NO 3
<211> LENGTH: 23
<212> TYPE: DNA
<213> ORGANISM: Artificial Sequence
<220> FEATURE:
<223> OTHER INFORMATION: /note="synthetic construct"

<400> SEQUENCE: 3
acccagggta gctttgcctt cat                                              23

<210> SEQ ID NO 4
<211> LENGTH: 21
<212> TYPE: DNA
<213> ORGANISM: Artificial Sequence
<220> FEATURE:
<223> OTHER INFORMATION: /note="synthetic construct"

<400> SEQUENCE: 4
gtacatcatg ggcaccttaa c                                                21

<210> SEQ ID NO 5
<211> LENGTH: 19
<212> TYPE: PRT
<213> ORGANISM: Artificial Sequence
<220> FEATURE:
<223> OTHER INFORMATION: /note="synthetic construct"

<400> SEQUENCE: 5

```
Asn Leu Glu Leu Gly Leu Thr Gln Ser Phe Ala Phe Ile His Lys
1               5                  10                  15

Asp Phe Asp Val
```

<210> SEQ ID NO 6
<211> LENGTH: 40
<212> TYPE: PRT
<213> ORGANISM: Artificial Sequence
<220> FEATURE:
<223> OTHER INFORMATION: /note="synthetic construct"

<400> SEQUENCE: 6

```
Met Ser Arg Ser Thr Gln Glu Leu Leu Gly Tyr His Cys Arg Leu
1               5                  10                  15

Gln Asp Lys Leu Gln Glu Gln Glu Gly Ser Leu Ala Ala Glu Gly
                20                  25                  30

Arg His Ser Leu Ala Ser Ala Ala Asp His
                35                  40
```

<210> SEQ ID NO 7
<211> LENGTH: 2466

<212> TYPE: DNA
<213> ORGANISM: Artificial Sequence
<220> FEATURE:
<223> OTHER INFORMATION: /note="synthetic construct"

<400> SEQUENCE: 7

```
ctggagtggg gtaagaggcg aattatagac acaaggggct cctctgcagg         50
aaggaggcca agggaaagag gcttgaaagg cttgatattt cacccaccac        100
cactcactgc cggagtaagc aggtctcccc ttcccagggc tgaggggagg        150
cagggatgtg tgctgtccca gggctgagaa gtggcaggtg agctggtgat        200
tccttactgc ccaggttcgt tctaggaagg tgcgtcctca ccatgctgga        250
tggtgtccta gtccaggagc accccctgag ctcctggcct agactccaaa        300
gggttgggta gatgagcaaa gactttacaa agaccttagg cgatatatgt        350
ccaggagcac ccaggaatta ctgggctacc actgcagact gcaggacaag        400
ctccaagaac aggaaggaag tcttgcagct gaagggaggc actccttggc        450
```

```
ctccgcagcc gat cac atg aag gtg gtg cca agt ctc ctg ctc         493
            Met Lys Val Val Pro Ser Leu Leu Leu
             -20              -15 tcc gtc ctc ctg gca cag gtg tgg ctg gta ccc ggc ttg gcc         535
Ser Val Leu Leu Ala Gln Val Trp Leu Val Pro Gly Leu Ala
    -10              -5              -1  1 ccc agt cct cag tcg cca gag acc cca gcc cct cag aac cag         577
Pro Ser Pro Gln Ser Pro Glu Thr Pro Ala Pro Gln Asn Gln
         5               10              15 acc agc agg gta gtg cag gct ccc aag gag gaa gag gaa gat         619
Thr Ser Arg Val Val Gln Ala Pro Lys Glu Glu Glu Glu Asp
             20              25              30 gag cag gag gcc agc gag gag aag gcc agt gag gaa gag aaa         661
Glu Gln Glu Ala Ser Glu Glu Lys Ala Ser Glu Glu Glu Lys
                 35              40 gcc tgg ctg atg gcc agc agg cag cag ctt gcc aag gag act         703
Ala Trp Leu Met Ala Ser Arg Gln Gln Leu Ala Lys Glu Thr
 45              50              55 tca aac ttc gga ttc agc ctg ctg cga aag atc tcc atg agg         745
Ser Asn Phe Gly Phe Ser Leu Leu Arg Lys Ile Ser Met Arg
 60              65              70 cac gat ggc aac atg gtc ttc tct cca ttt ggc atg tcc ttg         787
His Asp Gly Asn Met Val Phe Ser Pro Phe Gly Met Ser Leu
         75              80              85 gcc atg aca ggc ttg atg ctg ggg gcc aca ggg ccg act gaa         829
Ala Met Thr Gly Leu Met Leu Gly Ala Thr Gly Pro Thr Glu
             90              95             100 acc cag atc aag aga ggg ctc cac ttg cag gcc ctg aag ccc         871
Thr Gln Ile Lys Arg Gly Leu His Leu Gln Ala Leu Lys Pro
                105             110 acc aag ccc ggg ctc ctg cct tcc ctc ttt aag gga ctc aga         913
Thr Lys Pro Gly Leu Leu Pro Ser Leu Phe Lys Gly Leu Arg
115             120             125 gag acc ctc tcc cgc aac ctg gaa ctg ggc ctc aca cag ggg         955
Glu Thr Leu Ser Arg Asn Leu Glu Leu Gly Leu Thr Gln Gly
         130             135             140 agt ttt gcc ttc atc cac aag gat ttt gat gtc aaa gag act         997
Ser Phe Ala Phe Ile His Lys Asp Phe Asp Val Lys Glu Thr
             145             150             155 ttc ttc aat tta tcc aag agg tat ttt gat aca gag tgc gtg        1039
Phe Phe Asn Leu Ser Lys Arg Tyr Phe Asp Thr Glu Cys Val
```

-continued

|  |  |  |  |  |  |  |  |  |  |  |  |  |  |
|--|--|--|--|--|--|--|--|--|--|--|--|--|--|
|  |  | 160 |  |  |  | 165 |  |  |  | 170 |  |  |  |
| cct | atg | aat | ttt | cgc | aat | gcc | tca | cag | gcc | aaa | agg | ctc | atg | 1081 |
| Pro | Met | Asn | Phe | Arg | Asn | Ala | Ser | Gln | Ala | Lys | Arg | Leu | Met |  |
|  |  |  | 175 |  |  |  |  | 180 |  |  |  |  |  |  |
| aat | cat | tac | att | aac | aaa | gag | act | cgg | ggg | aaa | att | ccc | aaa | 1123 |
| Asn | His | Tyr | Ile | Asn | Lys | Glu | Thr | Arg | Gly | Lys | Ile | Pro | Lys |  |
| 185 |  |  |  |  | 190 |  |  |  |  | 195 |  |  |  |  |
| ctg | ttt | gat | gag | att | aat | cct | gaa | acc | aaa | tta | att | ctt | gtg | 1165 |
| Leu | Phe | Asp | Glu | Ile | Asn | Phe | Glu | Thr | Lys | Leu | Ile | Leu | Val |  |
|  | 200 |  |  |  |  | 205 |  |  |  |  | 210 |  |  |  |
| gat | tac | atc | ttg | ttc | aaa | ggg | aaa | tgg | ttg | acc | cca | ttt | gac | 1207 |
| Asp | Tyr | Ile | Leu | Phe | Lys | Gly | Lys | Trp | Leu | Thr | Pro | Phe | Asp |  |
|  |  | 215 |  |  |  |  | 220 |  |  |  |  | 225 |  |  |
| cct | gtc | ttc | acc | gaa | gtc | gac | act | ttc | cac | ctg | gac | aag | tac | 1249 |
| Pro | Val | Phe | Thr | Glu | Val | Asp | Thr | Phe | His | Leu | Asp | Lys | Tyr |  |
|  |  |  | 230 |  |  |  |  | 235 |  |  |  |  | 240 |  |
| aag | acc | att | aag | gtg | ccc | atg | atg | tac | ggt | gca | ggc | aag | ttt | 1291 |
| Lys | Thr | Ile | Lys | Val | Pro | Met | Met | Tyr | Gly | Ala | Gly | Lys | Phe |  |
|  |  |  |  | 245 |  |  |  |  | 250 |  |  |  |  |  |
| gcc | tcc | acc | ttt | gac | aag | aat | ttt | cgt | tgt | cat | gtc | ctc | aaa | 1333 |
| Ala | Ser | Thr | Phe | Asp | Lys | Asn | Phe | Arg | Cys | His | Val | Leu | Lys |  |
| 255 |  |  |  |  | 260 |  |  |  |  | 265 |  |  |  |  |
| ctg | ccc | tac | caa | gga | aat | gcc | acc | atg | ctg | gtg | gtc | ctc | atg | 1375 |
| Leu | Pro | Tyr | Gln | Gly | Asn | Ala | Thr | Met | Leu | Val | Val | Leu | Met |  |
|  | 270 |  |  |  |  | 275 |  |  |  |  | 280 |  |  |  |
| gag | aaa | atg | ggt | gac | cac | ctc | gcc | ctt | gaa | gac | tac | ctg | acc | 1417 |
| Glu | Lys | Met | Gly | Asp | His | Leu | Ala | Leu | Glu | Asp | Tyr | Leu | Thr |  |
|  |  | 285 |  |  |  |  | 290 |  |  |  |  | 295 |  |  |
| aca | gac | ttg | gtg | gag | aca | tgg | ctc | aga | aac | atg | aaa | acc | aga | 1459 |
| Thr | Asp | Leu | Val | Glu | Thr | Trp | Leu | Arg | Asn | Met | Lys | Thr | Arg |  |
|  |  |  | 300 |  |  |  |  | 305 |  |  |  |  | 310 |  |
| aac | atg | gaa | gtt | ttc | ttt | ccg | aag | ttc | aag | cta | gat | cag | aag | 1501 |
| Asn | Met | Glu | Val | Phe | Phe | Pro | Lys | Phe | Lys | Leu | Asp | Gln | Lys |  |
|  |  |  |  | 315 |  |  |  |  | 320 |  |  |  |  |  |
| tat | gag | atg | cat | gag | ctg | ctt | agg | cag | atg | gga | atc | aga | aga | 1543 |
| Tyr | Glu | Met | His | Glu | Leu | Leu | Arg | Gln | Met | Gly | Ile | Arg | Arg |  |
| 325 |  |  |  |  | 330 |  |  |  |  | 335 |  |  |  |  |
| atc | ttc | tca | ccc | ttt | gct | gac | ctt | agt | gaa | ctc | tca | gct | act | 1585 |
| Ile | Phe | Ser | Pro | Phe | Ala | Asp | Leu | Ser | Glu | Leu | Ser | Ala | Thr |  |
|  | 340 |  |  |  |  | 345 |  |  |  |  | 350 |  |  |  |
| gga | aga | aat | ctc | caa | gta | tcc | agg | gtt | tta | caa | aga | aca | gtg | 1627 |
| Gly | Arg | Asn | Leu | Gln | Val | Ser | Arg | Val | Leu | Gln | Arg | Thr | Val |  |
|  |  | 355 |  |  |  |  | 360 |  |  |  |  | 365 |  |  |
| att | gaa | gtt | gat | gaa | agg | ggc | act | gag | gca | gtg | gca | gga | atc | 1669 |
| Ile | Glu | Val | Asp | Glu | Arg | Gly | Thr | Glu | Ala | Val | Ala | Gly | Ile |  |
|  |  |  | 370 |  |  |  |  | 375 |  |  |  |  | 380 |  |
| ttg | tca | gaa | att | act | gct | tat | tcc | atg | cct | cct | gtc | atc | aaa | 1711 |
| Leu | Ser | Glu | Ile | Thr | Ala | Tyr | Ser | Met | Pro | Pro | Val | Ile | Lys |  |
|  |  |  |  | 385 |  |  |  |  | 390 |  |  |  |  |  |
| gtg | gac | cgg | cca | ttt | cat | ttc | atg | atc | tat | gaa | gaa | acc | tct | 1753 |
| Val | Asp | Arg | Pro | Phe | His | Phe | Met | Ile | Tyr | Glu | Glu | Thr | Ser |  |
| 395 |  |  |  |  | 400 |  |  |  |  | 405 |  |  |  |  |
| gga | atg | ctt | ctg | ttt | ctg | ggc | agg | gtg | gtg | aat | ccg | act | ctc | 1795 |
| Gly | Met | Leu | Leu | Phe | Leu | Gly | Arg | Val | Val | Asn | Pro | Thr | Leu |  |
|  | 410 |  |  |  |  | 415 |  |  |  |  | 420 |  |  |  |
| cta | taa | ttcaggacac | gcataagcac | ttcgcgtgta | gtagatgctg |  |  |  |  |  |  |  |  | 1841 |
| Leu |  |  |  |  |  |  |  |  |  |  |  |  |  |  |
| 423 |  |  |  |  |  |  |  |  |  |  |  |  |  |  |
| aatctgaggt | atcaaacaca | cacaggatac | cagcaatgga | tggcagggga |  |  |  |  |  |  |  |  |  | 1891 |

-continued

```
gagtgttcct tttgttctta actagtttag ggtgttctca aataaataca        1941
gtagtcccca cttatctgag ggggatacat tcaaagaccc ccagcagatg        1991
cctgaaacgg tggacagtgc tgaacctTat atatattttt tcctacacat        2041
acatacctat gataaagttt aatttataaa ttaggcacag taagagatta        2091
acaataataa caacattaag taaaatgagt tacttgaatg caagcactgc        2141
aataccataa cagtcaaact gattatagag aaggctacta agtgactcat        2191
gggcgaggag catagacagt gtggagacat tgggcaaggg gagaattcac        2241
atcctgggtg ggacagagca ggacaatgca agattccatc ccactactca        2291
gaatggcatg ctgcttaaga cttttagatt gtttatttct ggaattttc         2341 atttaatgtt tttggaccat ggttgaccat ggttaactga gactgcagaa        2391
agcaaaacca tggataaggg aggactacta caaaagcatt aaattgatac        2441
atatttttta aaaaaaaaaa aaaaa                                   2466
```

<210> SEQ ID NO 8
<211> LENGTH: 444
<212> TYPE: PRT
<213> ORGANISM: Artificial Sequence
<220> FEATURE:
<223> OTHER INFORMATION: /note="synthetic construct"

<400> SEQUENCE: 8

```
Met Lys Val Val Pro Ser Leu Leu Leu Ser Val Leu Leu Ala
    -20             -15                 -10

Val Val Trp Leu Val Pro Gly Leu Ala Pro Ser Pro Gln Ser
         -5              -1  1               5

Pro Glu Thr Pro Ala Pro Gln Asn Gln Thr Ser Arg Val Val
            10                  15                  20

Gln Ala Pro Lys Glu Glu Glu Asp Glu Gln Glu Ala Ser
                25              30              35

Glu Glu Lys Ala Ser Glu Glu Lys Ala Trp Leu Met Ala
                40                  45

Ser Arg Gln Gln Leu Ala Lys Glu Thr Ser Asn Phe Gly Phe
50              55                  60

Ser Leu Leu Arg Lys Ile Ser Met Arg His Asp Gly Asn Met
        65              70                  75

Val Phe Ser Pro Phe Gly Met Ser Leu Ala Met Thr Gly Leu
            80              85                  90

Met Leu Gly Ala Thr Gly Pro Thr Glu Thr Gln Ile Lys Arg
                95              100                 105

Gly Leu His Leu Gln Ala Leu Lys Pro Thr Lys Pro Gly Leu
                    110                 115

Leu Pro Ser Leu Phe Lys Gly Leu Arg Glu Thr Leu Ser Arg
120             125                 130

Asn Leu Glu Leu Gly Leu Thr Gln Gly Ser Phe Ala Phe Ile
        135                 140                 145

His Lys Asp Phe Asp Val Lys Glu Thr Phe Phe Asn Leu Ser
            150                 155                 160

Lys Arg Tyr Phe Asp Thr Gly Cys Val Pro Met Asn Phe Arg
                165                 170                 175

Asn Ala Ser Gln Ala Lys Arg Leu Met Asn His Tyr Ile Asn
                    180                 185
```

```
Lys Glu Thr Arg Gly Lys Ile Pro Lys Leu Phe Asp Glu Ile
190                 195                 200

Asn Phe Glu Thr Lys Leu Ile Leu Val Asp Tyr Ile Leu Phe
    205                 210                 215

Lys Gly Lys Trp Leu Thr Pro Phe Asp Pro Val Phe Thr Glu
        220                 225                 230

Val Asp Thr Phe His Leu Asp Lys Tyr Lys Thr Ile Lys Val
            235                 240                 245

Pro Met Met Tyr Gly Ala Gly Lys Phe Ala Ser Thr Phe Asp
                250                 255

Lys Asn Phe Arg Cys His Val Leu Lys Leu Pro Tyr Gln Gly
260                 265                 270

Asn Ala Thr Met Leu Val Val Leu Met Glu Lys Met Gly Asp
    275                 280                 285

His Leu Ala Leu Glu Asp Tyr Leu Thr Thr Asp Leu Val Glu
        290                 295                 300

Thr Trp Leu Arg Asn Met Lys Thr Arg Asn Met Glu Val Phe
            305                 310                 315

Phe Pro Lys Phe Lys Leu Asp Gln Lys Tyr Glu Met His Glu
                320                 325

Leu Leu Arg Gln Met Gly Ile Arg Arg Ile Phe Ser Pro Phe
330                 335                 340

Ala Asp Leu Ser Glu Leu Ser Ala Thr Gly Arg Asn Leu Gln
    345                 350                 355

Val Ser Arg Val Leu Gln Arg Thr Val Ile Glu Val Asp Glu
        360                 365                 370

Arg Gly Thr Glu Ala Val Ala Gly Ile Leu Ser Glu Ile Thr
            375                 380                 385

Ala Tyr Ser Met Pro Pro Val Ile Lys Val Asp Arg Pro Phe
                390                 395

His Phe Met Ile Tyr Glu Glu Thr Ser Gly Met Leu Leu Phe
400                 405                 410

Leu Gly Arg Val Val Asn Pro Thr Leu Leu
    415                 420

<210> SEQ ID NO 9
<211> LENGTH: 53
<212> TYPE: PRT
<213> ORGANISM: Artificial Sequence
<220> FEATURE:
<223> OTHER INFORMATION: /note="synthetic construct"

<400> SEQUENCE: 9

Glu Arg Gly Thr Glu Ala Val Ala Gly Ile Leu Ser Glu Ile Thr
1               5                   10                  15

Ala Tyr Ser Met Pro Pro Val Ile Lys Val Asp Arg Pro Phe His
                20                  25                  30

Phe Met Ile Tyr Glu Glu Thr Ser Gly Met Leu Leu Phe Leu Gly
                35                  40                  45

Arg Val Val Asn Pro Thr Leu Leu
                50

<210> SEQ ID NO 10
<211> LENGTH: 53
<212> TYPE: PRT
<213> ORGANISM: Artificial Sequence
```

```
<220> FEATURE:
<223> OTHER INFORMATION: /note="synthetic construct"

<400> SEQUENCE: 10

Glu Arg Gly Thr Glu Val Val Ser Gly Thr Val Ser Glu Ile Thr
1               5                   10                  15

Ala Tyr Cys Met Pro Pro Val Ile Lys Val Asp Arg Pro Phe His
                20                  25                  30

Phe Ile Ile Tyr Glu Glu Met Ser Arg Met Leu Leu Phe Leu Gly
            35                  40                  45

Arg Val Val Asn Pro Thr Val Leu
            50

<210> SEQ ID NO 11
<211> LENGTH: 53
<212> TYPE: PRT
<213> ORGANISM: Artificial Sequence
<220> FEATURE:
<223> OTHER INFORMATION: /note="synthetic construct"

<400> SEQUENCE: 11

Glu Lys Gly Thr Glu Ala Ala Gly Ala Met Phe Leu Glu Ala Ile
1               5                   10                  15

Pro Met Ser Ile Pro Pro Glu Val Lys Phe Asn Lys Pro Phe Val
                20                  25                  30

Phe Leu Met Ile Glu Gln Asn Thr Lys Ser Pro Leu Phe Met Gly
            35                  40                  45

Lys Val Val Asn Pro Thr Gln Lys
            50

<210> SEQ ID NO 12
<211> LENGTH: 53
<212> TYPE: PRT
<213> ORGANISM: Artificial Sequence
<220> FEATURE:
<223> OTHER INFORMATION: /note="synthetic construct"

<400> SEQUENCE: 12

Glu Lys Gly Thr Glu Ala Thr Gly Ala Pro His Leu Glu Glu Lys
1               5                   10                  15

Ala Trp Ser Lys Tyr Gln Thr Val Met Phe Asn Arg Pro Phe Leu
                20                  25                  30

Val Ile Ile Lys Glu Tyr Ile Thr Asn Phe Pro Leu Phe Ile Gly
            35                  40                  45

Lys Val Val Asn Pro Thr Gln Lys
            50

<210> SEQ ID NO 13
<211> LENGTH: 56
<212> TYPE: PRT
<213> ORGANISM: Artificial Sequence
<220> FEATURE:
<223> OTHER INFORMATION: /note="synthetic construct"

<400> SEQUENCE: 13

Glu Glu Gly Ser Glu Ala Ala Ala Ser Thr Ala Val Val Ile Ala
1               5                   10                  15

Gly Arg Ser Leu Asn Pro Asn Arg Val Thr Phe Lys Ala Asn Arg
                20                  25                  30

Pro Phe Leu Val Phe Ile Arg Glu Val Pro Leu Asn Thr Ile Ile
            35                  40                  45
```

```
Phe Met Gly Arg Val Ala Asn Pro Cys Val Lys
            50                  55

<210> SEQ ID NO 14
<211> LENGTH: 53
<212> TYPE: PRT
<213> ORGANISM: Artificial Sequence
<220> FEATURE:
<223> OTHER INFORMATION: /note="synthetic construct"

<400> SEQUENCE: 14

Glu Glu Gly Thr Gln Ala Thr Thr Val Thr Thr Val Gly Phe Met
1               5                   10                  15

Pro Leu Ser Thr Gln Val Arg Phe Thr Val Asp Arg Pro Phe Leu
                20                  25                  30

Phe Leu Ile Tyr Glu His Arg Thr Ser Cys Leu Leu Phe Met Gly
                35                  40                  45

Arg Val Ala Asn Pro Ser Arg Ser
                50

<210> SEQ ID NO 15
<211> LENGTH: 50
<212> TYPE: PRT
<213> ORGANISM: Artificial Sequence
<220> FEATURE:
<223> OTHER INFORMATION: /note="synthetic construct"

<400> SEQUENCE: 15

Glu Asp Gly Thr Lys Ala Ser Ala Ala Thr Thr Ala Ile Leu Ile
1               5                   10                  15

Ala Arg Ser Ser Pro Pro Trp Phe Ile Val Asp Arg Pro Phe Leu
                20                  25                  30

Phe Phe Ile Arg His Asn Pro Thr Gly Ala Val Leu Phe Met Gly
                35                  40                  45

Gln Ile Asn Lys Pro
                50

<210> SEQ ID NO 16
<211> LENGTH: 12
<212> TYPE: PRT
<213> ORGANISM: Artificial Sequence
<220> FEATURE:
<223> OTHER INFORMATION: /note="synthetic construct"

<400> SEQUENCE: 16

Leu Ala Pro Ser Pro Gln Ser Pro Glu Thr Pro Ala
1               5                   10
```